US008865236B2

(12) United States Patent
Katevas et al.

(10) Patent No.: US 8,865,236 B2
(45) Date of Patent: *Oct. 21, 2014

(54) SOLVENT-FREE PROCESS FOR OBTAINING PHOSPHOLIPIDS AND NEUTRAL ENRICHED KRILL OILS

(71) Applicant: Tharos Ltd., Santiago (CL)

(72) Inventors: Dimitri Sclabos Katevas, Santiago (CL); Raül R. Toro Guerra, Santiago (CL); Mario Chiong Lay, Santiago (CL)

(73) Assignee: Tharos Ltd., Santiago (CL)

( * ) Notice: Subject to any disclaimer, the term of this patent is extended or adjusted under 35 U.S.C. 154(b) by 0 days.

This patent is subject to a terminal disclaimer.

(21) Appl. No.: 14/074,992

(22) Filed: Nov. 8, 2013

(65) Prior Publication Data

US 2014/0065236 A1    Mar. 6, 2014

Related U.S. Application Data

(62) Division of application No. 13/504,011, filed as application No. PCT/IB2009/007269 on Oct. 30, 2009, now Pat. No. 8,609,157.

(51) Int. Cl.
| A01N 65/00 | (2009.01) |
| A61Q 19/00 | (2006.01) |
| C11B 13/00 | (2006.01) |
| A23L 1/30 | (2006.01) |
| A61K 8/92 | (2006.01) |
| C11B 1/06 | (2006.01) |
| A61K 35/56 | (2006.01) |
| A23D 9/013 | (2006.01) |
| C11B 1/02 | (2006.01) |
| A23D 9/007 | (2006.01) |
| C11B 1/16 | (2006.01) |
| A61K 8/55 | (2006.01) |
| A61Q 1/12 | (2006.01) |
| A61Q 1/10 | (2006.01) |
| A61Q 1/06 | (2006.01) |

(52) U.S. Cl.
CPC .............. *A61K 35/612* (2013.01); *A61Q 19/00* (2013.01); *A61Q 1/12* (2013.01); *C11B 13/00* (2013.01); *A23L 1/3006* (2013.01); *A61K 8/925* (2013.01); *C11B 1/06* (2013.01); *A23D 9/013* (2013.01); *A61Q 1/10* (2013.01); *C11B 1/02* (2013.01); *A61Q 1/06* (2013.01); *A23D 9/007* (2013.01); *C11B 1/16* (2013.01); *A61K 8/553* (2013.01)
USPC ........................................................ 424/725

(58) Field of Classification Search
None
See application file for complete search history.

(56) References Cited

U.S. PATENT DOCUMENTS

| 4,119,619 A | 10/1978 | Vasilievich et al. |
| 6,800,299 B1 | 10/2004 | Beaudoin et al. |
| 7,666,447 B2 | 2/2010 | Rockway |
| 7,838,050 B2 | 11/2010 | Randolph et al. |
| 7,906,153 B2 | 3/2011 | Theoharides |
| 7,977,498 B2 | 7/2011 | Wang |
| 2004/0234587 A1 | 11/2004 | Sampalis |
| 2004/0241249 A1 | 12/2004 | Sampalis |
| 2005/0192634 A1 | 9/2005 | Beaudoin |
| 2007/0122452 A1 | 5/2007 | Moriguchi et al. |
| 2007/0213298 A1 | 9/2007 | Rongved et al. |
| 2008/0031826 A1 | 2/2008 | Odegaard et al. |
| 2008/0113046 A1 | 5/2008 | Gardette |
| 2008/0166420 A1 | 7/2008 | Sones |
| 2008/0200707 A1 | 8/2008 | Shimano et al. |
| 2008/0226682 A1 | 9/2008 | Brake et al. |
| 2008/0248187 A1 | 10/2008 | Schoerken et al. |
| 2008/0254135 A1 | 10/2008 | Heuer et al. |
| 2008/0274203 A1 | 11/2008 | Bruheim et al. |
| 2009/0061067 A1 | 3/2009 | Tilseth et al. |
| 2009/0099261 A1 | 4/2009 | Bell et al. |
| 2009/0182050 A1 | 7/2009 | Barrow |
| 2009/0258081 A1 | 10/2009 | Minatelli et al. |
| 2009/0291102 A1 | 11/2009 | Fortin |
| 2009/0292019 A1 | 11/2009 | Fortin |
| 2009/0317532 A1 | 12/2009 | Bromley et al. |
| 2010/0041622 A1 | 2/2010 | Bromley et al. |
| 2010/0055191 A1 | 3/2010 | Arakawa et al. |
| 2010/0055281 A1 | 3/2010 | Barrow et al. |
| 2010/0062057 A1 | 3/2010 | Berge et al. |
| 2010/0081836 A1 | 4/2010 | Parslow et al. |
| 2010/0119600 A1 | 5/2010 | Opheim |
| 2010/0130761 A1 | 5/2010 | Boam et al. |
| 2010/0143571 A1 | 6/2010 | Breivik |
| 2010/0227792 A1 | 9/2010 | Tilseth et al. |

(Continued)

FOREIGN PATENT DOCUMENTS

| DE | 202010011127 U1 | 10/2010 |
| EP | 1127497 A | 8/2001 |

(Continued)

OTHER PUBLICATIONS

Office Action from the corresponding Japanese Patent Application No. 2012-535941 dated Feb. 4, 2014.

(Continued)

*Primary Examiner* — Michael Meller
(74) *Attorney, Agent, or Firm* — Lucas & Mercanti, LLP

(57) ABSTRACT

The invention discloses a new solvent-free process for obtaining phospholipids and neutral lipids enriched krill oils containing DHA and EPA poly-unsaturated fatty acids and astaxanthin. The process includes cooking fresh krill at high temperature—without agitation and or grinding; decanting the cooked krill for obtaining a partial de-fatted and de-watered solid and a liquid; squeezing the obtained solid to obtain a press liquid and a solid fraction; centrifuging the press liquid to obtain the phospholipids enriched krill oil; centrifuging of the decanter liquid obtained to obtain the neutral lipid enriched krill oil and stickwater.

13 Claims, 3 Drawing Sheets

(56) References Cited

U.S. PATENT DOCUMENTS

| | | |
|---|---|---|
| 2010/0239715 A1 | 9/2010 | Beaudoin et al. |
| 2010/0291053 A1 | 11/2010 | Clayton et al. |
| 2010/0291206 A1 | 11/2010 | Klaveness et al. |
| 2010/0310728 A1 | 12/2010 | Van Lengerich |
| 2011/0014327 A1 | 1/2011 | Testa |
| 2011/0015154 A1 | 1/2011 | Kellermann et al. |
| 2011/0020316 A1 | 1/2011 | Minatelli et al. |
| 2011/0028434 A1 | 2/2011 | Destaillats et al. |
| 2011/0033595 A1 | 2/2011 | Krumbholz et al. |
| 2011/0033602 A1 | 2/2011 | Martinsen |
| 2011/0045555 A1 | 2/2011 | Kralovec et al. |

FOREIGN PATENT DOCUMENTS

| | | |
|---|---|---|
| EP | 2248798 A1 | 11/2010 |
| FR | 2859380 A1 | 3/2005 |
| GB | 407729 A | 3/1934 |
| GB | 2465988 A | 6/2010 |
| JP | 58126756 A | 7/1983 |
| JP | 02215351 A | 8/1990 |
| WO | 8606082 A | 10/1986 |
| WO | 0023546 A | 4/2000 |
| WO | 02102394 | 12/2002 |
| WO | 2007054197 A1 | 5/2007 |
| WO | 2007080514 A2 | 7/2007 |
| WO | 2007080515 A1 | 7/2007 |
| WO | 2008050219 A2 | 5/2008 |
| WO | 2008060163 | 5/2008 |
| WO | 2008117062 A1 | 10/2008 |
| WO | 2008/140026 | 11/2008 |
| WO | 2008142482 A2 | 11/2008 |
| WO | 2009017425 A1 | 2/2009 |
| WO | 2009027692 A2 | 3/2009 |
| WO | 2009121839 | 10/2009 |
| WO | 2009132463 A1 | 11/2009 |
| WO | 2009134147 A1 | 11/2009 |
| WO | 2009139641 A1 | 11/2009 |
| WO | 2010006765 A1 | 1/2010 |
| WO | 2010035013 A1 | 4/2010 |
| WO | 2010038964 A2 | 4/2010 |
| WO | 2010097701 A1 | 9/2010 |
| WO | 2010106571 A1 | 9/2010 |
| WO | 2010128401 A1 | 11/2010 |
| WO | 2010136900 A2 | 12/2010 |
| WO | 2010137939 A1 | 12/2010 |

OTHER PUBLICATIONS

Yanase M., "Modification of a Russian method for separation of heat-coagulated protein from Antarctic krill," International Food Information Service, 1974.

Tou Janet C., et al., "Krill for human consumption: nutritional value and potential heath benefits," Nutrition Reviews, Feb. 2007, vol. 65, No. 2, pp. 63-77.

Yamaguchi K., et al., "Supercritical carbon dioxide extraction of oils from antarctic kril," Journal of Agricultural and Food Chemistry, Jan. 1986, vol. 34, No. 1, pp. 904-907.

Martin A. "Antarctic Krill," Phytotherapie, Aug. 2007, vol. 5, No. 1, pp. 6-13.

Fricke, H., et al., "1-O-Alkylglycerolipids in Antarctic Krill (*Euphausia superba* Dana)," 1986, vol. 85B, No. 1, pp. 131-134.

Gordeev K., et al., "Fatty Acid Composition of the Main Phospholipids of the Antarctic Krill *Euphausia superba*," Khimiya Prirodnykh Soedinenii, Mar.-Apr. 1990, No. 2, pp. 181-187.

SOLVENT-FREE PROCESS FOR OBTAINING PHOSPHOLIPIDS AND NEUTRAL ENRICHED KRILL OILS

CROSS-REFERENCE TO RELATED APPLICATIONS

This application is a divisional of U.S. patent application Ser. No. 13/504,011, filed Apr. 25, 2012, which in turn is a 371 of PCT/IB2009/007269, filed Oct. 30, 2009, the contents of each of which are incorporated herein by reference.

TECHNICAL FIELD

The present invention relates to processes for obtaining krill oil with polyunsaturated fatty acid DHA and EPA in the phospholipids fraction, with astaxanthin, and neutral lipids coming from the meal processing line, used for human health applications while the resulting krill meal will have a low fat content. This invention also discloses a procedure for obtaining a dried complex that contains krill oil in combination with phospholipids linked to DHA and EPA, proteins and astaxanthin for the use on human health human applications.

BACKGROUND ART

Krill corresponds to a group of small and abundant marine crustaceans in the order Euphasiaceae, living in the pristine Antarctic Ocean that is considered the feed base of all the Antarctic eco-system. The Antarctic krill, in particular those that live at the Antarctic and sub-Antarctic regions, are composed of 11 *Euphasia* species, being dominant *Euphausia superba*, Dana and *Euphausia crystallorophias*.

In recent years, krill has acquired great interest as a potential source of protein and other active biological products (Ellingsen, T. and Mohr, V. 1979. Process Bioch. 14:14; Suzuki, T. 1981. Fish and krill protein processing technology. London, Applied Science Publishers). The large expectation ciphered in the South Antarctic krill is based on the large biomass in the Antarctic ocean, which is estimated to be between 100 to 500 millions tons. It has been suggested that captures of krill could reach up to 50-100 millions tons/year, a quantity that is equivalent to the total fish capture in the world (Budzinski, E., Bykowski, P. and Dutkiewicz, D. 1986. Posibilidades de elaboración y comercialización de productos preparados a partir de krill del Antartico, FAO Doc. T, c. Pesca (268):47 p).

There are several publications related to the krill lipid content and composition (Grantham, G. J. 1977. The Southern Ocean. The utilization of Krill. Southern Ocean Fisheries Survey Programme, Rome. FAO GLO/SO/77/3:63 p; Budzinski et al. 1986. Loc. cit.; Ellingsen and Mohr. 1979. Loc. cit.). The lipid content is about 10-26% of the krill dry weight, depending on the season of the year and its sexual maturity as well as body size. Usually the krill fatty period is between March to June each year. The female krill has near double the amount of lipids than the male. The lipid concentration increases with age and decreases rapidly after the spawning. Krill lipids distribution studies showed that lipid rich areas are located along the digestive tract, between the muscle bundles and under the exoskeleton (Saether, O., Ellingsen, T. and Mohr, V. 1985. Compo Biochem. Physiol. 81B:609).

The main krill lipid fractions include triglycerides, phospholipids, as well as its sterols and esters (Grantham. 1977. Loc. cit.; Budzinski et al. 1986. Loc. cit.). The average content of phospholipids is about 69% and triglycerides about 26%. The krill phospholipids fraction, rich in polyunsaturated fatty acids, particularly 20:5 and 22:6, correspond to approximately 50% of total phospholipids.

There are several publications describing Krill lipid composition. The following being the most relevant among them:
1. Gordeev et al. described that *E. superba* contains about 5% of its natural weight of extractable lipids, more than half of which are in the form of phospholipids—phosphatidylcholine (33-36% of the lipids total), phosphatidylethanolamine (15-17%), lysophosphatidylcholine (3-4%), others (2-3%)—while triacylglycerols predominate (32-35%) among the phosphorus-free components. In the first two phospholipids the dominating fatty acid residue is the arachidonic acid residue (more than 40% of the acyl residues total) and the amount of eicosapentaenoic acid residues (C20:5w3) are about 13 and 28%, respectively. (Gordeev, K. Y. et al. 1990. Fatty acid composition of the main phospholipids of the Antarctic krill *Euphausia superb*. Chemistry of Natural Compounds. 26: 143-147).
2. Fricke et al. described that *Euphausia superba* Dana lipid composition was phosphatidylcholine (33-36%), phosphatidylethanolamine (5-6%), triacylglycerol (33-40%), free fatty acids (8-16%) and sterols (1.4-1.7%). Wax esters and sterol esters were present only in traces. More than 50 fatty acids could be identified and the major ones being 14:0, 16:0, 16:1(n-7), 18:1(n-9), 18:1(n-7), 20:5(n-3) and 22:6(n-3). Phytanic acid was found in a concentration of 3% of total fatty acids. Short, medium-chain and hydroxy fatty acids (C≤0) were not detectable. The sterol fraction consisted of cholesterol, desmosterol and 22-dehydrocholesterol. (Fricke, H. et al. 2006. Lipid, sterol and fatty acid composition of Antarctic krill (*Euphausia superba* Dana). Lipids, 19:821-827).
3. Falk-Petersen et al described that lipids of Arctic and Antarctic euphausiids show a seasonally-dependent high lipid content, and neutral lipids, whether wax esters or triacylglycerols, are primarily accumulated for reproduction. The Arctic *Thysanoessa inermis* and the Antarctic *Euphausia crystallorophias* contain high levels of wax esters and higher concentrations of 18:4(n-3) and 20:5(n-3) and a lower ratio of 18:1(n-9)/(n-7) fatty acids in their neutral lipids than those in the Arctic *Thysanoessa raschii* and the Antarctic *Thysanoessa macrura* and *Euphausia superba*. Large amounts of phytol in the lipids of *T. raschii* and *E. crystallorophias* during winter suggest the ingestion of decaying algae originated from sedimenting material or in sea ice. *Thysanoessa raschii*, *T. macrura*, and *E. superba* have a high ratio of 18:1(n-9)/(n-7) fatty acids, indicating animal carnivory (Falk-Petersen, S. et al. 2000. Lipids, trophic relationships, and biodiversity in Arctic and Antarctic krill. Can. J. Fish. Aquat. Sci. 57: 178-191).
4. Clarke described lipid content and composition of the Antarctic krill *Euphausia superba*. Female total lipid content increases during the summer as the ovary matures, and there is also some evidence of an increase in the lipid content of males and immatures as winter approaches. The storage lipid is mainly triacylglycerol and there is less than 1% wax ester. Fatty acids are moderately unsaturated, though less so in the ovarian lipid, and the triacylglycerol contains up to 4% phytanic acid (Clarke A. 1984. Lipid content and composition of Antarctic krill, *Euphausia superba* Dana. J. Crust. Biol. 4:285-294).
5. Phleger et al. described lipid compositions of Antarctic euphausiids, *Euphausia superba, E. tricantha, E. frigida* and *Thysanoessa macrura* collected near Elephant Island during 1997 and 1998. Total lipid was highest in *E. superba* small juveniles (16 mg g–1 wet mass), ranging from 12 to 15 mg in other euphausiids. Polar lipid (56-81% of total lipid) and triacylglycerol (12-38%) were the major lipids with wax esters (6%) only present in *E. tricantha*. Cholesterol was the major sterol (80-100% of total sterols) with desmosterol second in abundance (1-18%). 1997 *T. macrura* and *E. superba* contained a more diverse sterol profile, including 24-nordehydrocholesterol (0.1-1.7%), trans-dehydrocholesterol (1.1-1.5%), brassicasterol (0.5-1.7%), 24-methylenecholesterol (0.1-0.4%) and two stanols (0.1-0.2%). Monounsaturated fatty acids included primarily 18:1(n-9)c (7-21%), 18:1(n-7)c (3-13%) and 16:1 (n-7)c (2-7%). The main saturated fatty acids in krill were 16:0(18-29%), 14:0 (2-15%) and 18:0 (1-13%). Highest eicosapentaenoic acid [EPA, 20:5(n-3)] and docosahexaenoic acid [DHA, 22:6(n-3)] occurred in *E. superba* (EPA, 15-21%; DHA, 9-14%), and were less abundant in other krill. Lower levels of 18:4(n-3) in *E. tricantha*, *E. jrigida* and *T. macrura* (0.4-0.7% of total fatty acids) are more consistent with a carnivorous or omnivorous diet as compared with herbivorous *E. superba* (3.7-9.4%). The polyunsaturated fatty acid (PUFA) 18:5(n-3) and the very-long chain (VLC-PUFA), C(26) and C(28) PUFA, were not present in 1997 samples, but were detected at low levels in most 1998 euphausiids (phleger, C.F. 2002. Interannual and between species comparison of the lipids, fatty acids and sterols of Antarctic krill from the US AMLR Elephant Island survey area. Comp Biochem Physiol B Biochem Mol Biol. 131:733-747).
6. Kolakowska described lipid compositions of seven krill (*Euphausia superba* D.) samples, fresh and after various periods of storage at 251K (Kelvin Degrees). Fresh krill lipid composition differed from that determined in frozen samples, depending on storage duration, season of harvest, and developmental stage. Phospholipids proved most susceptible to changes, as opposed to triglycerides, which were most resistant; diglycerides and cholesterol esters were also destroyed. The freezing process per-se affected the lipid composition only slightly; however, after 30 days storage the amount of free fatty acids almost doubled. After 6 months storage at 251° K, 70% of phospholipids were decomposed and the amount of free fatty acids increased by a factor of 6 to 20. Monoglycerides, absent from fresh krill, appeared after several months of frozen storage. Juvenile krill were more susceptible to lipolytic changes. Females bearing mature eggs contained stable phospholipids; only triglycerides were hydrolysed (Kolakowska A. 1986. Lipid composition of fresh and frozen-stored krill. Z Lebensm Unters Forsch. 182:475-478.
7. Bottino described lipid compositions of two Antarctic euphausiids. In *Euphausia superba* complex lipids were the major lipid class followed by triglycerides. In *E. crystallorophias* the complex lipids were also the major lipid class, but the second major constituent was wax. The complex lipids of both Euphausiids consisted mostly of phosphatidylcholine with smaller amounts of phosphatidylethanolamine and lysophosphatidylcholine. The phospholipids of *E. crystallorophias* were less unsaturated than those of *E. superba*. The waxes of *E. crystallorophias* were mostly esters of oleic (84%) and palmitoleic (10%) acids with n-tetradecanol (69%) and n-hexadecanol (28%) (Bottino, N. R. 1975. Lipid composition of two species of Antarctic krill: *Euphausia superba* and *E. crystallorophias*. Comp Biochem Physiol B. 50:479-484).
8. EP1997498 and WO02/102394 owned by Neptune Technologies & Bioressources Inc. Relate to Neptune krill oil that corresponds to acetone extracted krill lipids. Proteins and krill material are removed from the lipid extract through filtration. The acetone and residual water are removed by evaporation. The phospholipids content is 38-50%, and EPA and DHA is 22-35%, wherein the major amount of these omega-3's are attached to phospholipids.
9. US2008/0274203 and WO 20081117062 owned by Aker Biomarine ASA. These applications disclose a new krill oil composition characterized by high amounts of phospholipids, astaxanthin esters and/or omega-3. This krill oil is characterized by comprising about 30-60% w/w phospholipids and about 20-35% omega-3 fatty acid wherein the major amount of these omega-3 lipids are attached to phospholipids.

The high content of polyunsaturated fatty acids in the phospholipidic fraction could be necessary to keep the plasmatic membrane fluidity at low temperatures in the Antarctic oceans. A high unsaturation level might be required to give the krill phospholipids deposits the necessary plasticity for the animal flectation and motion at low temperatures.

An increase of the total lipids present in the krill is accompanied with both a decrease in the phospholipids and an increase in the triglycerides. The polyunsaturated fatty acid content decreases as the content of total lipids increase (Saether et al. 1985. Loc. cit.). Post-mortem changes that occur in krill lipids showed that during the krill storage at 0° C. the polyunsaturated fatty acids (20:5, 22:6) compared to the content of fatty acids (16:0) do not decrease. These data suggest that during the krill storage at 0° C. a large oxidation of polyunsaturated fatty acids after the crustacean death does not occur.

There are several documents describing industrial processes to obtain krill oil. These documents are:
1. Budzinski et al. (1986. Loc. cit.) and Saether et al. (1985. Loc. cit.), described procedures for krill lipid extraction with different organic solvents.
2. CA2346979, ES2306527 or UA75029, documents presented by Universite de Sherbrooke. This document described a method to extract lipid fraction from marine and aquatic animals, including krill, using acetone extraction.
3. WO2006/106325 presented by Pro-Bio Group AS. This document described a process to obtain phospholipids from krill. This process comprises contacting the krill meal with an organic solvent to produce a lipid containing liquid. Optionally this liquid is extracted with other organic solvents to extract neutral lipids. The remaining fraction is a phospholipids enriched fraction.
4. EP1997498 and WO02/102394 presented by Neptune Technologies & Bioressources Inc. These documents describe lipid extraction from krill or krill derived material utilizing ketone solvents, preferably acetone.
5. GB407729 presented by Johan Olsen Nygaard. This patent describes a method to extract oil from marine animals, in particular whale and other sea mammals, by heating in bath of oil. This document is different from our invention because is not applied to krill and utilizes heated oil for lipid extraction. Our invention does not use heated oil for phospholipids extraction.

These five documents describe the utilization of organic solvents, particularly acetone, to extract krill lipid fractions. These methods being different from the procedure disclosed herein, as the method declared in the present invention does not utilize organic solvents for extracting or purifying lipid fractions from Antarctic krill.
1. JP58008037, Nippon Suisan Kaisha Ltd. This document describes a method to obtain eicosapentaenoic acid or derivatives from Antarctic krill oil. Krill oil is converted into free fatty acid or an ester thereof by the conventional method, e.g. saponification or alcoholysis, being the resultant product continuously distilled to collect a main fraction of distillate containing 40 wt % or more titled substance. The main fraction of distillate is then treated with urea to remove low unsaturated fatty acids. This document differs from the present invention through the use of a distillation process for lipid purification.
2. JP2004024060 (Nippon Suisan Kaisha Ltd). This document describes a procedure for obtaining an astaxanthin enriched lipid fraction from Antarctic krill. This document declares a different process from the one declared in the present invention in that the instant process aim is not the astaxanthin production.
3. US2005/0274203 (Aker Biomarine ASA). This document describes a procedure for obtaining krill oil from krill meal using supercritical fluid extraction in a two-stage process. Stage 1 removes the neutral lipid by extracting with neat supercritical $CO_2$ or $CO_2$ plus approximately 5% of a co-solvent. Stage 2 extracts the actual krill oils by using supercritical $CO_2$ in combination with approximately 20% ethanol. This document differs from the present invention as this procedure does not use supercritical fluid extraction.
4. WO2007/080514 (Krill A/S and Alfa Laval Copenhagen A/S), describes a method for extracting lipid fractions from krill, wherein freshly captured krill is grinded to obtain a slurry, which is gently heated to a temperature below 60° C., preferably bellow 30° C., for less than 45 minutes, thereafter the liquid splits into an aqueous phase and a krill oil phase from which a krill oil extract is derived without the use of organic solvents. This document reveals a process different from the one declared in the instant invention as the present procedure does not grind the captured krill before heating. This document is also different since the heating temperature declared in the instant process is >90° C. Another main difference regarding the process declared in this document is that grinded krill used to produce slurry before heating produces an emulsification that impedes the phospholipids separation by centrifugation. In the present invention a slurry is not directly or indirectly produced. Further in WO2007/080514 is used ultrasound for krill oil separation while the present invention does not use any type of ultrasound technology. It also proposes a simple extraction while the present invention is based in a double-extraction principle.
5. WO2007080515 (Aker Biomarine ASA) describes a process for obtaining krill lipids by processing the krill at a temperature below 60° C. with mechanical and physical disruption of the lipid cell membrane to facilitate low temperature extraction. This process takes place under inert gas atmosphere to prevent oxidation or denaturation of fat and proteins. Intermediate processing tanks are kept at a minimum level to reduce residence time; and the oil after recovery is immediately frozen to stabilize it. This document differs from the present invention since the instant procedure does not grind the captured krill to facilitate lipid extraction, instead a heating temperature of >90° C. is used; further the process of the present invention does not use any type of gases or freezing technologies.
6. WO2008/060163 (Pronova Biopharma Norge AS), describes a procedure for obtaining krill oil-using $CO_2$ at supercritical pressure containing ethanol, methanol, propanol or isopropanol. This document is different from the present invention because the present procedure does not use $CO_2$ supercritical lipid extraction with or without solvent.
7. WO2009/027692 (Aker Biomarine ASA), describes a method for krill meal production. This procedure uses a two-step cooking process. In the first step the proteins and phospholipids are removed from the krill and precipitated as a coagulum. In the second stage the krill without phospholipids are cooked. Following this, residual fat and astaxanthin are removed from the krill using mechanical separation methods. In this method, krill is heated to 60-75° C. in the presence of water to dissolve/disperse lipids and proteins to the water phase, called krill milk. This krill milk was heated to 95-100° C. to remove as a precipitate the krill protein and lipids from the water phase. The processes of the present invention differ from those disclosed in this document since the krill oil is not separated from the crustacean by precipitation and the multiple heating steps are avoided.

From current traditional krill meal processing on board, in some factory vessels, only a small amount of krill oil is produced. This krill oil is usually enriched in neutral lipids with very low or undetectable amount of phospholipids (0.5%). Normally, during the traditional on board krill process, fresh krill is heated using an indirect heating cooker with rotating screw conveyor, followed by a twin-screw press and drier. The press liquid obtained by the twin-screw press is passed through a decanter to remove the insoluble solids. The clarified decanter liquid is then used to feed separators centrifuges to separate the krill oil normally enriched with neutral lipids and astaxanthin. In this traditional process the phospholipids are bound to the proteins in the press cake. Therefore, phospholipids are usually found associated to the krill meal. In the krill fatty period, the fat content in the krill meal is usually 16-18%. In the same krill fatty period, the yield of the neutral lipid-enriched krill oil obtained using the traditional krill meal plant is low, ranging usually between 0.3-1.0% from raw krill. This neutral lipid-enriched krill oil contains astaxanthin ranging between 700-1,500 mg/kg depending on the season and the fishing ground catching.

Moreover, when a non-traditional krill meal processing layout is used, a similar situation explained above was obtained. Normally, the non-traditional krill meal plant considered a contherm cooker system, a two-phase decanter or three-phase decanter and a drier. These decanters are used for de-watering and de-fatting the cooked krill. The decanter liquid is used to feed the centrifuge separators to obtain usually a neutral lipid-enriched krill oil with low or undetectable levels of phospholipids (0.5%). In this case, the phospholipids are also bound to the proteins in the decanter solids. As described above, phospholipids are found in the krill meal.

In this case, the yield of neutral lipid-enriched krill oil from the non-traditional krill meal plant is much lower, in the fatty period ranging from 0.1 to 0.4% of raw krill. In this process a conventional contherm cooker system is used which has inherent agitation (scraped knife). Therefore, the processed krill is agitated and also minced. This agitation/mincing process produce lipid emulsification along with krill proteins and water. Besides, krill phospholipids catalyze the emulsification because these lipids act as an emulsifier agent. For this reason, using a non-traditional krill meal process, higher lipid content is bound to the decanter solids. In the krill fatty period, the fat content of the decanter liquid has a lipid content ranging from 1.0 to 2.5%, the resultant stick water has a yellow color and it is emulsified, with a fat content ranging from 0.7 to 1.6%, the krill meal has a fat content ranging from 20 to 26%, and the krill oil recovery by this nontraditional process is very low.

The lipid composition and fatty acid profile of neutral lipid-enriched krill oil obtained using the traditional and non-traditional krill meal processing are very similar: triglycerides about 86-89%, phospholipids not detected (0.5%), and DHA and EPA about 4-6%.

Several efforts have been made to produce a krill meal with a lower fat content and phospholipids enriched krill oil containing DHA and EPA, through an industrial scale method associated to a krill meal plant. Several different cooking temperatures, different decanting torque, strong pressing, using two decanting steps, washing the first decanter solids with stick water before the second decanter, electroplasmolysis and so on have been tested. However, the results have not been successful.

Focusing on the problem to separate phospholipids-enriched krill oil with DHA and EPA, some extraction methods have been developed and patent protected.

The patent application CL 1021 1995 (Compañía Tepual S.A) refers to a method for obtaining krill oil using thermal fractionation and centrifugation. This oil obtaining process claims that the fatty acids types and lipids composition can be regulated controlling the krill cooking temperature during the process of oil production. At high cooking temperature (95° C.) lower yield of poly-unsaturated and phospholipids fractions were obtained as compared when the cooking temperature was reduced (75° C.). Also this oil process claims that main components of its fractional composition correspond to triglycerides being 35 to 96%; and phospholipids from 4 to 28%. The poly-unsaturated fatty acids ranged from 4 to 46%. Basically this process used for obtaining krill oil, considers krill cooking, pressing the cooked krill and the passing the press liquid through a two-phase decanter to separate the insoluble solids, being the oil separated from the decanter liquid using centrifuge separator. During this process only one type of krill oil was obtained.

SUMMARY OF THE INVENTION

This invention discloses a new on board (at sea) and/or on shore (on land) process for simultaneously obtaining both: 1) phospholipids enriched krill oil and 2) neutral lipid enriched krill oil containing DHA and EPA poly-unsaturated fatty acids and astaxanthin. Antarctic krill oil is particularly rich in DHA and EPA containing phospholipids. Because the amphipathic nature of phospholipids, i.e. a negative charged phosphate group in one end and a hydrophobic lipid in the other end, this lipid is a very potent emulsifier agent. Krill grinding and/or mincing induce emulsification of soluble proteins, water, neutral lipids and phospholipids. Therefore, once the emulsion is formed, phospholipids can be obtained from krill mixtures only by organic solvent or $CO_2$ supercritical extractions. See WO021102394 and US2008/0274203 as example.

In the present invention a new procedure for phospholipids extraction from fresh krill or other similar crustaceans is disclosed. This procedure is based on a process where no grinding, agitation and/or mincing of the krill is carried out. Using this method substantially no phospholipids-catalyzed emulsification occurs. Cooking of whole intact krill or fraction produces the release of a liquid from the crustaceans. The oil contained in this liquid is enriched with neutral lipids. The whole and intact krill was further squeezed to obtain a new liquid fraction. The oil obtained by centrifugation of this second fraction is enriched in phospholipids. The resultant squeezed krill is used to obtain a low fat krill meal.

The present invention allows a much more efficient extraction process and is preferably done almost immediately after raw or fraction of krill has been captured at sea. The present invention, which is preferably done onboard, which allows having a much more controlled extraction process, allowing a dramatic reduction in not-necessary logistic transshipment, raw material and cargo handling. Other advantages of the present invention include the "finished product" character of the end product which is obtained on the same premises where capture and processing takes place.

The process of the present invention can also be used with other similar crustacean species whether they are farmed or captured crustaceans, such as but not limited to *Pandalus borealis, Cervimunidajohni, Heterocarpus reedi, Pleuroncodes monodom, Penaeus vannamei, Penaeus monodon, Penaeus stylirostris, Penaeus chinensis, Penaeus. orientalis, Penaeus japonicus, Penaeus in dicus, Penaeus merguiensis, Penaeus esculentus, Penaeus setiferus, Macrobrachium* spp, and others.

Therefore, the process disclosed in this invention includes the steps of:

a) cooking whole fresh krill and/or a fraction thereof at high temperature for protein denaturation, without agitating, grinding and/or mincing in this step, neither in further processing steps;

b) decanting the cooked krill from step a) using a decanter with high torque to obtain a partially de-fatted and de-watered solid and a decanter liquid;

c) squeezing the partially de-fatted and de-watered solid from step b) through a press to obtain a press liquid and a solid fraction;

d) centrifuging the press liquid from step c) to obtain krill oil enriched in phospholipids;

e) centrifuging the decanter liquid from step b) to obtain krill oil enriched in neutral lipids, and stick water; and f) optionally, drying the press liquid from step c) to obtain a dried complex of human-grade krill which contains krill oil in combination with phospholipids, DHA, EPA, proteins and astaxanthin.

As a part of the present innovation, this invention also discloses the use of special equipment, wherein such equipment is designed to avoid agitation, mincing, and/or grinding, throughout all processing steps (i.e. cooking, pumping, and so on) to reduce oil emulsification with protein, water and krill phospholipids, this last component acting as the emulsifier agent. Such equipment includes screw pumps, continuous cookers with screw conveyor at low speed, belt conveyors, screw conveyors, de-boner, chopper or similar.

Other special equipment possible to use, that has been designed to avoid agitation and/or grinding, throughout all processing steps include:

1. Krill and other crustaceans peeling machines;
2. Krill and other crustaceans brush peeling machines;
3. Krill and other crustaceans disk peeling machines;
4. Krill and other crustaceans coagulator machines working at low speed;
5. Krill and other crustaceans dewatering machines working at low speed; and
6. Krill and other crustaceans deboning machines.

Krill oils obtained using the procedure disclosed in the present invention include the neutral lipid-enriched krill oil separation from the decanter liquid obtained by using specific centrifuge separators. These centrifuge separators are specifically and only used for the decanter liquid treatment. The phospholipids-enriched krill oil is obtained from the press liquid using other specially-designed centrifuge separators. The decanter removes important neutral lipids into the decanter liquid while the phospholipids are more concentrated in the decanter cake. Therefore, each krill oil type has its own exclusive processing line composed of separators centrifuges, pumps, piping, tanks, heat exchangers and packaging station.

This invention relates to a method for obtaining specific Krill oils from Krill, preferably from South Antarctic Krill, through a processing preferably made on board (at sea), on board factory trawlers, or mother vessels. Further, the present invention is suitable for being carried out on shore (on land) processing plants. The final processing target of the processing method disclosed in this invention includes: a) cooking of whole or fraction fresh marine species without agitation and/or mincing; b) decanting of cooked marine species using a two-phase decanter and/or a three-phase decanter or any other type of decanting solution with high torque to obtain a partial de-fatted and de-watered solid and a decanter liquid; c) squeezing of the partial de-fatted and de-watered decanter solid through a simple press and/or using a twin-screw press and/or any other pressing solution to obtain a press liquid and a solid fraction which was further processed to obtain the low fat dried marine-species meal; d) centrifuging of the press liquid to obtain the phospholipids enriched marine-species oil; e) centrifuging of the decanter liquid obtained in step b) to obtain the neutral lipid enriched marine-species oil and stick water. The equipment used in this process allows avoiding agitation throughout all steps (i.e. cooking, pumping, and so on) to reduce oil emulsification with protein, water and marine species phospholipids, acting this last component as the emulsifier agent.

This invention also includes phospholipids-, neutrallipids-, omega-3's- and proteinenriched dried powder, and the use of this product as a heath product for human application, a powerful health-promoter, growth enhancer, immune-system promoter and wellness end-product. All products obtained with the procedure disclosed in this invention are produced by a non-chemical treatment, i.e. a process free of organic solvents and/or $CO_2$ supercritical fluid, for separating the krill oil.

The phospholipids enriched krill oil of the present invention is useful for human health application and has a total phospholipids content of about 30 to 70% w/w, preferably from about 35 to 60% w/w, and more preferably from about 35 to 55% w/w. The DHA and EPA content are from about 10 to 70% w/w, preferably from about 15 to 60% w/w, and more preferably from 20 to 55% w/w. Neutral lipids content is from 30 to 70% w/w, preferably from about 40% to 65% w/w, and more preferably from about 45 to 65% w/w. Astaxanthin content is from about 200 to 1,500 mg/kg, preferably from about 300 to 1,200 mg/kg, and more preferably from about 400 to 1,000 mg/kg.

The neutral lipid enriched krill oil of the present invention is also useful for human health application, having a content of neutral lipids from 50 to 100% w/w, preferably from 60 to 100% w/w, and more preferably from 70 to 100% w/w. DHA and EPA content are from 2 to 45% w/w, preferably from 2 to 40% w/w, and more preferably from 5 to 35% w/w. Phospholipids content is less than 10% w/w, preferably less than 5% w/w, and more preferably less than 2% w/w. Astaxanthin content is from 200 to 1,500 mg/kg, preferably from 300 to 1200 mg/kg, and more preferably from 400 to 1,000 mg/kg.

The phospholipids-enriched krill oil of the present invention is preferably produced on board (at sea) which provides having the direct advantage of using of a fresh raw krill, this way avoiding freezing of the whole or fraction raw of krill. In addition to the freshness of the said end material, on board processing also produces fresh krill meal, which can eventually be used for further krill oils extraction processes in on shore (on land) processing plants.

These preferably on board (at sea) krill oil processing methods have additional and important advantages such as avoiding frozen raw krill transportation from at Sea operations (on board) to on shore (on land) port facilities and further transportation to on shore (on land) processing plants, this way the end-products of present invention have a significantly lower cost structure.

The phospholipids-enriched krill oil of the present invention is produced preferably using on board (at sea) processes. That means the assurance of the use of highly fresh whole or fraction raw krill, avoiding phospholipids decomposition and/or lipids deterioration which may occur during certain freezing process, frozen transportation and frozen storage typically required when prior art processes are carried-out on land (on shore) premises.

This invention represents a potent krill-related environment-driven development, as among its direct benefits, it includes:

a) An overall lower catch-volume requirement to secure the same amount output of end product as compared to other methods as there is a more efficient processing which allows less captured-tonnage per end-product-tonnage;
b) a significant reduction in processing infrastructure in relation to any other comparable processing method as the amount of catch and equivalent processing capacity is diminished due to the onboard processing;
c) a relevant improvement of the end-product quality in terms of freshness and its molecules quality, which means that the benefit to the end-user, be it for human health or animal nutrition, will be through the reduction of the market-cost per equivalent high-quality molecule;
d) this invention guarantees lower processing costs which goes to the direct benefit of end users through a lower end-product selling price;
e) the biomass protection is also guaranteed as the value-added concept is secured on board (at sea) and does not need extra costs to transport raw material for further on shore (on land) processing;
f) This invention allows having end-products secured on board (at sea); and
g) This invention will also provide a much better resource protection as the catch effort will not be focused on a limited catch and processing period rather spread-out the entire krill fishing season.

This invention further relates to South Antarctic Krill processing made preferably on board (at sea) factory trawlers or mother vessels. This invention also relates to krill processing made on shore (on land) processing plants whereas the on board (at sea) processing steps prevails on shore (on land). The final processing target of the processing method disclosed in this invention includes:

a) cooking of whole and fresh marine species without agitation and or grinding;
b) decanting of cooked marine species using a two-phase decanter and/or a three-phase decanter and/or any other type of decanting solution with high torque to obtain a partial de-fatted and de-watered solid and a decanter liquid;
c) squeezing of the partial de-fatted and de-watered decanter solid through a simple press and/or using a twin-screw press and/or any other pressing solution to obtain a press liquid and a solid fraction which was further processed to obtain the low fat dried marine-species meal;
d) centrifuging of the press liquid to obtain the phospholipids enriched marine-species oil; and
e) centrifuging of the decanter liquid obtained in step b) to obtain the neutral lipid enriched marine-species oil and stick water.

This process uses equipment that avoid or substantially avoid agitation throughout all steps (i.e. cooking, pumping, and so on) to reduce oil emulsification with protein, water and marine-species phospholipids, which act as the emulsifier agent.

The on board (at sea) processing includes either on board factory trawlers, mother vessels acting as processors only, mother vessels acting as catchers and processors or any other combination for mother vessels, onboard tramper vessels used as processing factories and/or any other at sea processing factory vessel and/or any other at sea processing factory layout operation for this specific purposes, being the resulting marine oils obtained either as a by-product or as a final product or a combination of both.

The krill meal obtained with the process of the present invention has a fat content ranging from 5 to 15%, protein content from 60% to 70%, and moisture content from 6 to 10%.

Because both krill oil composition obtained in the present invention are not exposed to the use of any toxic or non-toxic chemicals during the process, the resulting krill oils of this invention could be safely used for human consumption according to the European Food Safety Authority (EFSA) (Scientific Opinion of the Panel on Dietetic Products Nutrition and Allergies on a request from the European Commission of the safety of "Lipid extract from *Euphausia superba*" as food ingredient. The EFSA Journal (2009). 938, 1-16).

Human health applications for the krill oils obtained in the present invention, can be, without limitation, for reducing premenstrual symptoms, preventing hypertension, control of blood glucose levels in patients, control of arthritis symptoms, prevention of hyperlipidemia and other health applications. Such oils can also be used in preparing dermatologic products, specially topic or systemic products, for treating skin diseases related to a deficiency of essential fatty acids, such as xerotic skin, hyperkeratosis, ictiosis, acne, dermic ulcers, psoriasis, serborreic eczema, atopic dermatitis, among others.

DETAILED DESCRIPTION OF THE INVENTION

Figure 1:
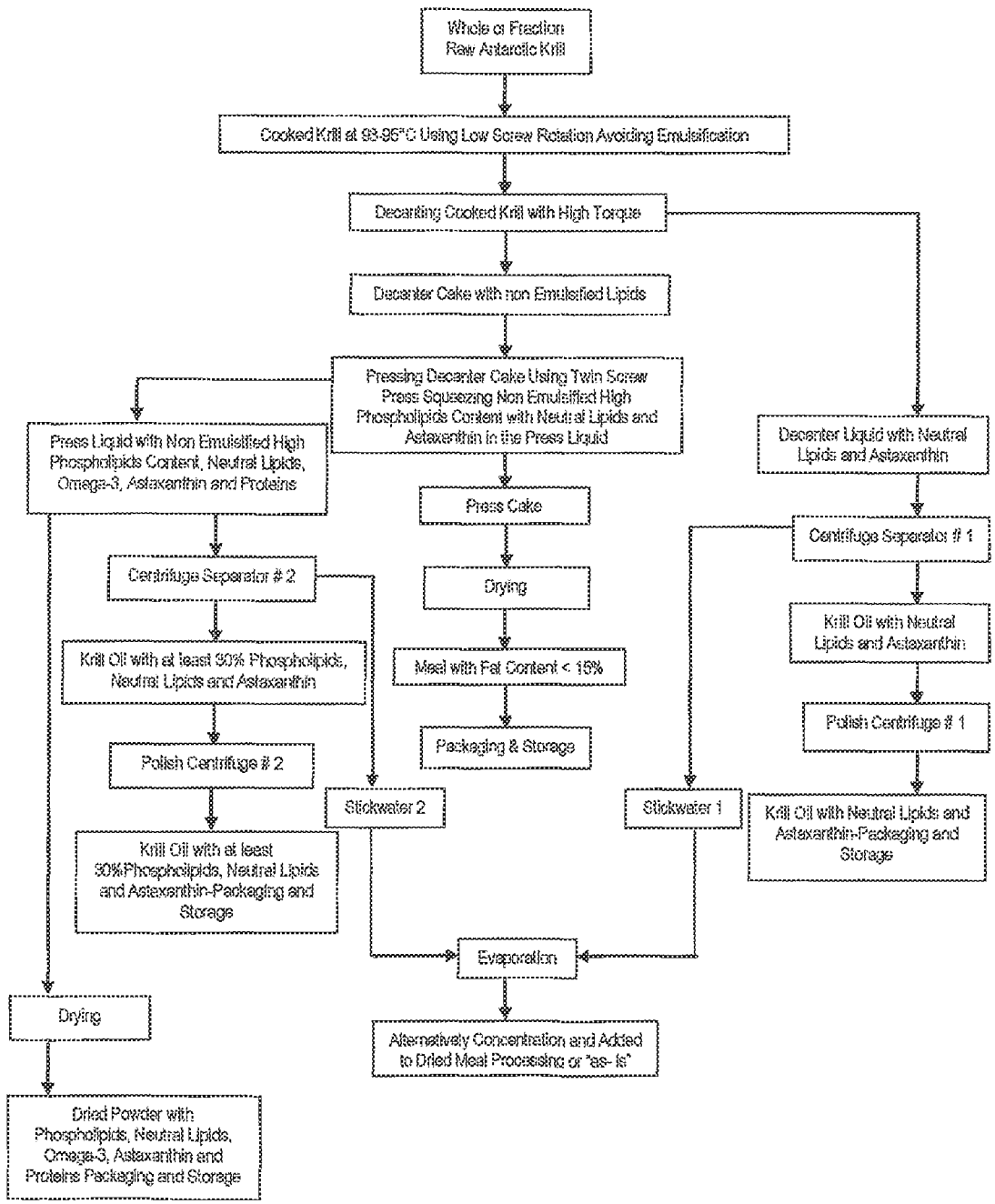
FIG. 1 is a flowchart depicting the process of the present invention.
Figure 2:
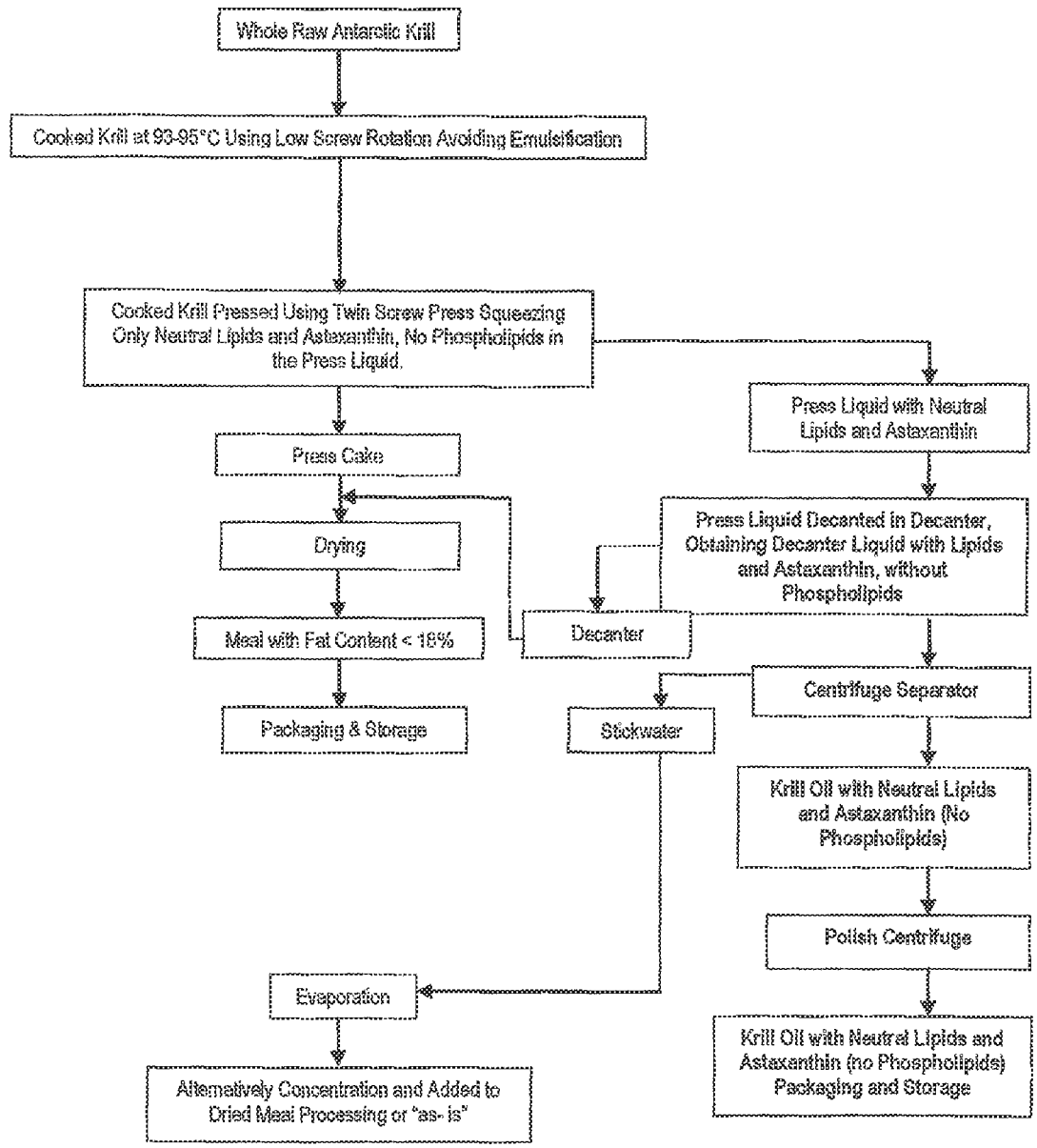
FIG. 2 shows the current processing layout using traditional process.
Figure 3:
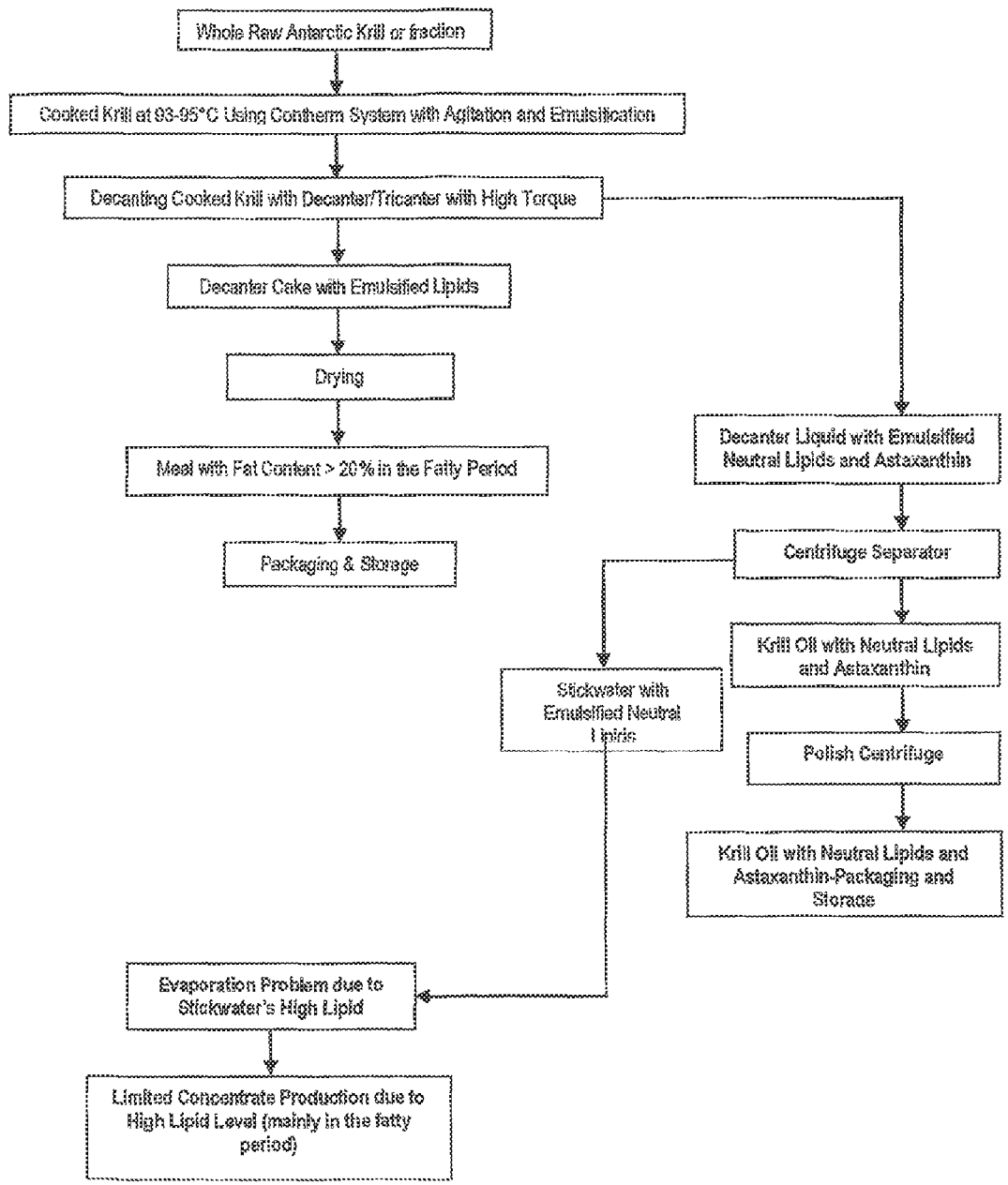
FIG. 3 shows the current processing layout using non-traditional process.

Before describing the present invention in detail, it should be understood that the invention as described is not to be limited in its application to the process details described herein. The invention as such, embraces other embodiments and various ways for being applied. It is also should be understood that the phraseology or terminology used herein is for the purpose of description and it is not intended for any type of limitation.

The present invention provides systems and processes for processing a marine biomass. As a preferred embodiment, the marine biomass is krill, preferably the Antarctic krill *Euphasia superba*. Other krill species or crustacean can also be processed using the systems and processes of the present invention. Examples of such species are *E. crystallorophias, E. frigida, E. tricantha, E. vellantini, E. lougirostris, E. lucens, E. similis, E. spinifera, E. recurva, E. pacifica, Thysanoessa macrura, T. vicinia, T. gregaria, T. raschii, T. inermis, Pandalus borealis, Cervimunida johni, Heterocarpus reedi* or *Pleuroncodes monodom*. The krill is preferably processed in a fresh state as defined herein. Frozen krill is not preferred to be used with the process of the present invention, as ice crystals formed during krill freezing which can disrupt anatomical structures of the crustacean. Destruction of tissues by freezing is a well established subject in the state of art (Whittaker D K. 1984. Mechanisms of tissue destruction following cryosurgery. Ann R Coll Surg Engl. 66:313-318). Tissue disruption could favor oil emulsification during processing and also phospholipids' deterioration during frozen storage. As a preferred embodiment, the krill is processed fresh on board a fishing vessel either factory trawler, mother factory vessels, or intermediate processor or similar or whatever other ship suitable to carry out the process of this invention within a term of 14, 12, 10, 8, 6, 5, 4, 3, or preferably 2 hours of catching krill. In some embodiments, the krill is processed on board a ship within 1 hour or preferably 0.5 hours or more preferably within 20 minutes after catching the krill. Within the embodiments of the present invention, it is included that the ship tows a trawl that is configured to catch the krill and/or that the ship receives its krill or other species from fishing vessels or other factory trawlers. The krill is then transferred from the trawl to the ship and processed, preferably immediately after krill catching. The trawl comprises (either a regular fishing gear composed of trawls and/or purse seining system and/or) a pumping system to pump the freshly caught krill from the trawl to the ship so the krill can be processed in a fresh state. In some embodiments the catch system, be it regular trawl or pump system, it is designed in such a manner that substantially no damage, (deterioration) grinding or mincing is done to the krill during the pumping from the trawl to the ship.

In a preferred embodiment, the fresh whole krill or fraction is transported to the cooker using belt conveyor, or screw conveyor or screw pumping or another transport system avoiding krill agitation to avoid the oil emulsification with protein and water. The whole krill is cooked (i.e., heated) in a cooker with indirect and/or direct steam heating or another heating system, but at a low rotation speed of about 1-100 rpm, preferably 2-20 rpm, and more preferably 5-10 rpm, without agitation to avoid the oil emulsification. The krill temperature at the exit of the cooker is about 20-100° C., preferably 50-100° C., more preferably 75-100° C. and even more preferably 93-95° C., or whatever other temperatures not disclosed here but that are necessary to reach complete protein denaturation. The cooker type is not particularly restricted but as preferred embodiment this cooker must operate without agitation for avoiding the emulsification state.

In some embodiments the cooked krill is transported to the two-phase decanter using a screw conveyor or a screw pumping, or another transporting system without krill agitation for avoiding oil emulsification. The cooked krill is passed through a two phase decanter with high torque of about 1-10 kNn, preferably 1.2-5 kNn, more preferably 1.5-3 kNm, even more preferably 1.8-2.5 kNm, and a speed of about 100-10,000 rpm, preferably 1000-8000 rpm, more preferably 2,000-5,000 rpm, even more preferably 3,000-4,600 rpm, for partial de-watering and partial de-fatting, separating it into a decanter solids phase and a decanter liquid phase. In some embodiments, a decanter type is not particularly restricted. The moisture content of decanter solid is about 40-80%, preferably, 50-70%, more preferably 55-67%, even more preferably 58-65%.

Table N° 1 shows the lipid and moisture content of decanter solids and decanter liquids, obtained with krill catch during fatty period using a previous cooker with indirect and direct steam heating with screw conveyor at low rotation speed. The decanter solid has a lipid content range of 19.8% to 22.4% wt dry base, so the resulting hill meal with 8% of moisture from this solid will have a lipid content of about 18.2% to 20.6%. These results show that a two-phase decanter alone is not enough to reach a good de-fatting of the cooked krill for obtaining more krill oil and krill meal with a fat content lower than 18%. Anyway, this decanter solids obtained from the previous cooker at a low speed has lower lipid content and non-emulsified lipids than the process wherein a contherm cooker is used.

In some embodiments of the present invention, using a cooker calibrated for a low rotation speed, the decanter liquid obtained in such cooker is not emulsified and has higher lipid content compared to the decanter liquid using a conventional contherm cooker.

Table N° 2 shows the lipid and moisture content of decanter solids and decanter liquid, wherein a contherm cooker has been previously used. This equipment is not preferred within the embodiments of this invention, as a large proportion of lipids remain in the decanter solids, and the lipids contained in the decanter liquid are emulsified. Krill oil recovery using this equipment was very low and the resulting krill meal has a high fat content, specifically over 20% when obtained in the krill fatty period.

As a preferred embodiment in the process of the present invention, the obtained decanter liquid is passed through a separator centrifuge and then through a purifier separator centrifuge, for obtaining stick water and a krill oil enriched with neutral lipids with astaxanthin and substantially free or without (or no detectable) phospholipids. The obtained stick water has a low fat content, with a maximum of about 0.3-0.5%, in a nonemulsified form suitable for further processing (concentrate production) and sludge.

In some embodiments, there is provided a process for obtaining the neutral lipid-enriched oil, which has an exclusive and separated line including: separator centrifuge, purifier separator centrifuge, pumps, piping, heat exchangers, tanks and packaging station.

In a preferred embodiment of the process of the present invention, the decanter solids phase are fed to a twin-screw press using a screw pump or a screw conveyor or other feeding system wherein agitation does not occur. The decanter solids phase are pressed using twin screw press with high pressing force or using another pressing system to release the oil with phospholipids linked to the denatured protein according to the production line for the product of the present invention. As a preferred embodiment the pressing step is carried out by continuous pressing at a full feeding condition using a 2-10 rpm speed, and more preferably 3-6 rpm and a decanter solids temperature feeding of 90-96° C. and more preferably 93-95° C. The pressing system is not particularly restricted. As described above, the decanter solids phase keeps all of the phospholipids inside of the coagulated protein, then a strong pressing of the decanter solids release an important percentage of the phospholipids to the press liquid. The moisture of this press cake is about 45-55%, preferably 48-53%. Table 3 shows the lipid and moisture content from the press cake of the present invention at different feeding levels of the twin press in the krill fatty period.

Table N° 4 shows this press liquid composition in the krill fatty period. According to the process or system disclosed in the present invention, this press liquid has a high fat content in the range of about 3-25%, preferably 5-20% and more preferably 8-17% (wet base), depending on the seasonal lipid content of krill and if it is not in an emulsified form. In the traditional krill meal processing using only a twin-screw press (without prior use of a decanter) the fat content in this press liquid is lower than 0.5-3% (wet base) depending on the lipid content of krill and if it is not in an emulsified form.

In some embodiments of the present invention, there is also provided a dried complex with oil containing phospholipids with DHA and EPA, proteins and astaxanthin obtained by drying the press liquid "as-is" without centrifuge separation. Such dried complex corresponds to a human-grade krill-related product for being used in many human health applications.

In some embodiments, a synergic action of the two-phase decanter and further pressing with twin-screw press or another strong pressing system is used to release the phospholipids with DHA and EPA in the oil, mixed with astaxanthin and neutral lipids. The press liquid, at a temperature of about 25-121° C., preferably 50-110° C., more preferably 80-100° C. and even more preferably 90-96° C., is pumped to the separator centrifuge, using a screw pump or other feeding system, avoiding agitation, wherein the krill oil with phospholipids with DHA and EPA mixed with astaxanthin and neutral lipids is separated. The processing speed in the centrifuge separator operates at 4,000-8,000 rpm, more preferably at 4,600-6,800 rpm, with an automatic periodic discharge of solids. In one embodiment of the present invention, the oil separator centrifuge is not particularly restricted, i.e. any centrifuge equipment satisfying the indicated conditions can be used. This krill oil is once more centrifuged through a purifier separator to clarify it, operating at a processing speed of 5,000-10,000 rpm, more preferably at 6,000-8,200 rpm, with an automatic periodic discharge of solids for later being packaged. In the embodiments of the present invention, the purifier separator centrifuge is not particularly restricted, i.e. any centrifuge equipment satisfying the indicated conditions can be used.

As an additional preferred embodiment, the krill oil with phospholipids with DHA and EPA mixed with astaxanthin and neutral lipids, product of the present invention, is obtained using an exclusive and separated oil process line including: a separator centrifuge, a purifier separator, pumps, piping, heat exchangers, tanks and a packaging station, completely different and separated from the other oil line with neutral lipid from the decanter liquid phase.

Examples 3 and 4 show the characteristics of krill oils obtained in the present invention:

I) the neutral lipid enriched krill oil of the present invention is also useful for human health application having a content of:
  neutral lipids from 50 to 100% w/w, preferably from 60 to 100% w/w, and more preferably from 70 to 100% w/w,
  DHA and EPA content are from 2 to 45% w/w, preferably from 2 to 40% w/w, and more preferably from 5 to 35% w/w,
  Phospholipids content is lower than 10% w/w, preferably lower than 5% w/w, and more preferably lower than 2% w/w, and
  Astaxanthin content is from 200 to 1,500 mg/kg, more specifically from 300 to 1,200 mg/kg, and even more specifically from 400 to 1,000 mg/kg.

II) the phospholipids enriched krill oil of the present invention can be useful for human health applications, having a content of:
  total phospholipids content from 30 to 70% w/w, preferably from 35 to 60% w/w, and more preferably from 35 to 55% w/w,
  DHA and EPA content is from 10 to 70% w/w, preferably from 15 to 60% w/w, and more preferably from 20 to 55% w/w,
  Neutral lipids content is from 30 to 70% w/w, preferably from 40% to 65% w/w, and more preferably from 45 to 65% w/w, and Astaxanthin content is from 200 to 1,500 mg/kg, preferably from 300 to 1,200 mg/kg, and more preferably from 400 to 1,000 mg/kg.

According to the above declared compositions for both oil products, obtained through the process of the present invention, these oils are suitable for health human applications.

From the above, considering the composition characteristics of this krill oil and the process for obtaining the same, it can be concluded that the process of the present invention provides a krill oil product containing DHA and EPA in the phospholipids fraction with astaxanthin and neutral lipids. The present invention provides for a different process, which is new and improved, regarding all those krill oils obtained through processes involving solvent extraction and/or using supercritical fluid extraction or through thermal fractionation and centrifugation; with the resulting krill meal, in any Antarctic krill season, having a maximum fat content of 15%, a minimum protein content of 60% for a maximum moisture content of 10%.

In some embodiments, krill oils obtained with the procedure disclosed in the present invention can be stabilized by the use of antioxidants and/or preservatives and/or with a nitrogen-barred layer. Moreover, such krill oils can be stored within plastic or metal containers, necessarily suitable for food-grade, pharmaceutical-grade and/or cosmetic/grade applications, in special stainless steel containers, at room temperature or refrigerated, suitably protected from light.

In some embodiments, the present invention provides uses of krill oils for preparing krill oil compositions for being used as a dietary supplement and/or nutraceutical product. This invention also discloses pharmaceutical compositions comprising an effective amount of krill oil and at least one pharmaceutically acceptable transporter, excipient, stabilizer, diluents and/or adjuvant. In some of the embodiments, said krill oil compositions are suitable as photoprotectors. Said photoprotectors can be formulated as tanning creams and/or tanning oils. In some of the embodiments, said krill oil can be used to enhance cosmetic products. Said cosmetic products are, but no limited to, moisture creams, powder make ups, powder eye shadows, cream eye shadows compact powders and lipsticks. In some of the embodiments, said krill oil compositions can be effectively used for decreasing cholesterol plasma levels, inhibiting platelet adhesion, inhibiting artery plaque formation, preventing hypertension, controlling arthritis symptoms, preventing skin cancer, enhancing transdermal transport, reducing the symptoms of premenstrual symptoms or controlling blood glucose levels in a patient. Furthermore, in some embodiments, nutraceuticals, pharmaceuticals and cosmetics comprising the phospholipids-enriched krill oil are also embraced by the present invention.

TABLE 1

Table 1. Lipid and moisture content of decanter solids and decanter liquids obtained with krill captured during South Antarctic's Krill fatty period using a cooker with indirect and direct steam heating system with screw conveyor operating at a low rotation speed

| Krill Material | Decanter Torque (kNm) | Krill Temperature (° C.) | Moisture (%) | Total Solids (%) | Lipids WB (%) | Lipids DB (%) |
|---|---|---|---|---|---|---|
| Decanter Solids | 2.0 | 94 | 63.1 | 36.9 | 7.3 | 19.8 |
| Decanter Liquid | | | 93.2 | 6.8 | 1.6 | 23.5 |
| Decanter Solids | 2.1 | 93 | 62.9 | 37.1 | 8.1 | 21.8 |
| Decanter Liquid | | | 92.7 | 7.3 | 1.8 | 24.7 |
| Decanter Solids | 2.0 | 94 | 61.6 | 38.4 | 7.8 | 20.3 |
| Decanter Liquid | | | 91.3 | 8.7 | 1.9 | 21.8 |
| Decanter Solids | 2.0 | 93 | 63.0 | 37.0 | 8.3 | 22.4 |
| Decanter Liquid | | | 91.1 | 8.9 | 1.9 | 21.3 |

WB: wet base
DB: dry base

TABLE 2

Table 2. Lipid and moisture content of decanter solids and decanter liquids obtained with krill captured during South Antarctic's Krill fatty period using a contherm cooker system

| Krill Material | Decanter Torque (kNm) | Krill Temperature (° C.) | Moisture (%) | Total Solids (%) | Lipids WB (%) | Lipids DB (%) |
|---|---|---|---|---|---|---|
| Decanter Solids | 2.1 | 95 | 63.1 | 36.9 | 8.7 | 23.6 |
| Decanter Liquid | | | 92.7 | 7.3 | 1.5 | 20.5 |
| Decanter Solids | 2.0 | 96 | 61.9 | 38.1 | 9.3 | 24.4 |
| Decanter Liquid | | | 92.1 | 7.9 | 1.7 | 21.5 |
| Decanter Solids | 2.0 | 94 | 63.0 | 37.0 | 8.4 | 22.7 |
| Decanter Liquid | | | 92.3 | 7.7 | 1.5 | 19.5 |
| Decanter Solids | 2.0 | 95 | 63.6 | 36.4 | 8.6 | 23.6 |
| Decanter Liquid | | | 92.8 | 7.2 | 1.7 | 23.6 |

WB: wet base
DB: dry base

TABLE 3

Table 3. Lipid and moisture content of the press cake of the present invention at different feeding levels of the twin press

| | Moisture (%) | Dry Solids (%) | Lipids WB (%) | Lipids DB (%) |
|---|---|---|---|---|
| Press Cake 1 | 58.1 | 41.9 | 8.6 | 20.5 |
| Press Cake 2 | 58.6 | 41.4 | 8.4 | 20.3 |
| Press Cake 3 | 56.9 | 43.1 | 8.0 | 18.5 |
| Press Cake 4 | 56.7 | 43.3 | 8.0 | 18.5 |
| Press Cake 5 | 54.6 | 45.4 | 7.4 | 16.3 |
| Press Cake 6 | 54.5 | 45.5 | 7.2 | 15.8 |
| Press Cake 7 | 54.3 | 45.7 | 5.5 | 12.0 |
| Press Cake 8 | 53.9 | 46.1 | 5.6 | 12.1 |

WB: wet base
DB: dry base

Comments

Press Cake samples 1 to 6 were taken when the press was not fully fed with decanter solids Press Cake samples 7 & 8 were taken when the press was fully fed with decanter solids

TABLE 4

Table 4. Press liquid composition with krill captured during South Antarctic's Krill fatty period

| Composition | Press Liquid 1 | Press Liquid 2 | Press Liquid 3 | Press Liquid 4 |
|---|---|---|---|---|
| Moisture (%) | 78.3 | 77.7 | 77.3 | 80.4 |
| Proteins (%) | 5.8 | 6.1 | 6.2 | 5.2 |
| Lipids (%) | 16.9 | 14.0 | 15.3 | 13.2 |

TABLE 5

Table 5. Fresh raw whole krill composition

| Compounds | Value |
|---|---|
| Moisture (%) | 77.2 |
| Proteins (%) | 13.7 |
| Lipids (%) | 5.3 |
| Ash (%) | 3.0 |
| Astaxanthin (mg/Kg) | 47 |

TABLE 6

Table 6. Composition of the liquid and press cake phases obtained by the twin-screw press

| Compounds | Press Liquid (%) | Press Cake (%) |
|---|---|---|
| Moisture | 77.7 | 54.5 |
| Proteins | 6.1 | 32.7 |
| Lipids | 14.0 | 6.0 |
| Ash | 0.9 | 4.6 |

EXAMPLES

The present invention will be described in more detail using examples. It should be understood that the present invention is not limited by the following Examples.

Example 1

Process to Obtain Krill Oils and Low Fat Krill Meal of the Present Invention

The description represents an example of the process of the present invention. In FIG. 1 there is depicted a flow diagram of this process. The process clearly does not involve the use of organic solvents and/or supercritical $CO_2$ fluid.

Antarctic krill was captured during the period of March to May, preferably during the month of May, within krill's fatty period in the Orkney Islands fishing ground, using a pumping catch system, the Krill arriving alive on board a factory vessel and being immediately processed. Table N° 5 shows the fresh raw whole krill composition used.

Whole krill was collected into bunkers to drain seawater and transported on belt conveyors to tanks from wherein it was pumped to the cooker using a screw pump.

The continuous cooker with screw conveyor used live steam to increase the krill temperature from about 0° C. to 93-95° C. The cooker screw conveyor speed was set at 7-8 rpm.

The cooked krill was then pumped to the two-phase decanter using a screw pump. The continuous working cooker with screw conveyor used live steam to increase the krill temperature from about 0° C. to 93-95° C. The cooker screw conveyor speed was set at 7-8 rpm. The cooked krill was pumped to a two-phase decanter.

The two-phase decanter operated at 3,100 rpm and a 2.0 kNm torque was used, resulting in a decanter liquid phase and a decanter solid phase. Table N° 1 shows the decanter liquid and decanter solid composition.

The decanter liquid phase was collected into tanks at a temperature of 93-96° C., from wherein it was pumped with a screw pump to the separator centrifuge at a speed set at 4,600 rpm and immediately thereafter passed to a purifier separator at a speed set at 6,100 rpm, for obtaining a krill oil with neutral lipids without phospholipids. Example 3 shows this neutral lipids oil composition and characteristics.

The decanter solid phase was pressed in a twin-screw press resulting in a press liquid phase and press cake phase. Table N° 6 shows the composition obtained from these two phases.

The press cake was dried until it reached a moisture content lower than 10% using a rotaplate drier. Example 5 shows the krill meal composition obtained from this test.

The press liquid at a temperature of 93-96° C. was pumped with a screw pump to a specific separator centrifuge at a speed set at 4,600 rpm and immediately thereafter to a specific purifier separator at a speed set 6,100 rpm, to separate the krill oil with phospholipids. Example 4 shows the composition characteristics of this krill oil with DHA and EPA linked to the phospholipids fraction obtained from the present experiment.

Example 2

Flow Diagram and Mass Balance of the Process to Obtain Krill Oils and Low Fat Krill Meal of the Present Invention This example shows an estimate mass balance of a production line for the product of the present invention when raw krill is within the season when fat content is high (estimated at 5%) although not necessarily the highest fat content found in raw South Antarctic Krill and without the addition or recovery of stick water.

The following tables are an estimated mass balance of the process of the present invention without stick water recovery, utilizing raw krill with average-high fat content (around 5% w/w).

TABLE 7

| Product | MT/Hr | Yield (%) |
|---|---|---|
| Krill Meal (without concentrate) | 1.63 | 16.3 |
| Krill Oil with Phospholipids | 0.22 | 2.2 |
| Krill Oil with Neutral Lipids | 0.07 | 0.7 |
| Total | 1.92 | 19.2 |

TABLE 8

| FRESH RAW WHOLE KRILL | Kg/Hr | (%) | Kg/Hr | (%) |
|---|---|---|---|---|
| DS | 1,800 | 18.0 | | |
| F | 500 | 5.0 | | |
| Phospholipids | | | 200 | 40.0 |
| Neutral Lipids | | | 295 | 59.0 |
| Cholesterol | | | 5 | 1.0 |
| M | 7,700 | 77.0 | | |
| Total | 10,000 | 100 | 500 | 100 |

TABLE 9

| DECANTER SOLIDS | Kg/Hr | (%) | Kg/Hr | (%) |
|---|---|---|---|---|
| DS | 1,386 | 28.7 | | |
| F | 401 | 8.3 | | |
| Phospholipids | | | 190 | 47.4 |
| Neutral Lipids | | | 208 | 51.9 |
| Cholesterol | | | 3 | 0.7 |
| M | 3,043 | 63.0 | | |
| Total | 4,830 | 100 | 401 | 100 |

TABLE 10

| PRESS CAKE | Kg/Hr | (%) | Kg/Hr | (%) |
|---|---|---|---|---|
| DS | 1,248 | 40.8 | | |
| F | 160 | 5.2 | | |
| Phospholipids | | | 104 | 65.0 |
| Neutral Lipids | | | 54 | 34.0 |
| Cholesterol | | | 2 | 1.0 |
| M | 1,652 | 54.0 | | |
| Total | 3,060 | 100 | 160 | 100 |

TABLE 11

| PRESS CAKE + SLUDGE | Kg/Hr | (%) | Kg/Hr | (%) |
|---|---|---|---|---|
| DS | 1,303 | 35.6 | | |
| F | 195 | 5.3 | | |
| Phospholipids | | | 121 | 62.4 |
| Neutral Lipids | | | 70 | 35.9 |
| Cholesterol | | | 3 | 1.7 |
| M | 2,162 | 59.1 | | |
| Total | 3,660 | 100 | 195 | 100 |

TABLE 12

| KRILL SOLUBLES | Kg/Hr | (%) |
|---|---|---|
| DS | 0 | 0.0 |
| F | 0 | 0.0 |
| M | 0 | 0.0 |
| Total | 0 | 0.0 |

TABLE 13

| FEED TO DRIERS RCD | Kg/Hr | (%) | Kg/Hr | (%) |
|---|---|---|---|---|
| DS | 1,303 | 35.6 | | |
| F | 195 | 5.3 | | |
| Phospholipids | | | 121 | 62.4 |
| Neutral Lipids | | | 70 | 35.9 |
| Cholesterol | | | 3 | 1.7 |
| M | 2,162 | 59.1 | | |
| Total | 3,660 | 100 | 195 | 100 |

TABLE 14

| KRILL MEAL | Kg/Hr | (%) | Kg/Hr | (%) |
|---|---|---|---|---|
| DS | 1,303 | 80.0 | | |
| F | 195 | 12.0 | | |
| Phospholipids | | | 121 | 62.4 |

TABLE 14-continued

| KRILL MEAL | Kg/Hr | (%) | Kg/Hr | (%) |
|---|---|---|---|---|
| Neutral Lipids | | | 70 | 35.9 |
| Cholesterol | | | 3 | 1.7 |
| M | 130 | 8.0 | | |
| Total | 1,628 | 100 | 195 | 100 |

TABLE 15

| | Kg/Hr |
|---|---|
| EVAPORATOR | 0 |

TABLE 16

| | Kg/Hr |
|---|---|
| EVAPORATED DRIERS RCD | 2,032 |

TABLE 17

| DECANTER LIQUID | Kg/Hr | (%) | Kg/Hr | (%) |
|---|---|---|---|---|
| DS | 414 | 8.0 | | |
| F | 99 | 1.9 | | |
| Phospholipids | | | 10 | 10.1 |
| Neutral Lipids | | | 87 | 87.9 |
| Cholesterol | | | 2 | 2.0 |
| M | 4,657 | 90.1 | | |
| Total | 5,170 | 100 | 99 | 100 |

TABLE 18

| OIL WITH NEUTRAL LIPIDS | Kg/Hr | (%) | Kg/Hr | (%) |
|---|---|---|---|---|
| Oil | 69 | 100 | | |
| Phospholipids | | | 0 | 0 |
| Neutral Lipids | | | 68 | 98.6 |
| Cholesterol | | | 1 | 1.4 |
| Total | 69 | 100 | 69 | 100 |

TABLE 19

| PRESS LIQUID | Kg/Hr | (%) | Kg/Hr | (%) |
|---|---|---|---|---|
| DS | 139 | 7.8 | | |
| F | 241 | 13.6 | | |
| Phospholipids | | | 86 | 35.7 |
| Neutral Lipids | | | 153 | 63.7 |
| Cholesterol | | | 1 | 0.6 |
| M | 1,391 | 78.6 | | |
| Total | 1,770 | 100 | 241 | 100 |

TABLE 20

| OIL WITH PHOSPHOLIPIDS | Kg/Hr | (%) | Kg/Hr | (%) |
|---|---|---|---|---|
| Oil | 220 | 100 | | |
| Phospholipids | | | 79 | 35.7 |

TABLE 20-continued

| OIL WITH PHOSPHOLIPIDS | Kg/Hr | (%) | Kg/Hr | (%) |
|---|---|---|---|---|
| Neutral Lipids | | | 140 | 63.7 |
| Cholesterol | | | 1 | 0.3 |
| Total | 220 | 100 | 219 | 100 |

TABLE 21

| SLUDGE 1 | Kg/Hr | (%) | Kg/Hr | (%) |
|---|---|---|---|---|
| DS | 41 | 10.5 | | |
| F | 18 | 4.5 | | |
| Phospholipids | | | 10 | 56.1 |
| Neutral Lipids | | | 7 | 38.3 |
| Cholesterol | | | 1 | 5.6 |
| M | 336 | 85.0 | | |
| Total | 395 | 100 | 18 | 100 |

TABLE 22

| SLUDGE 2 | Kg/Hr | (%) | Kg/Hr | (%) |
|---|---|---|---|---|
| DS | 14 | 6.8 | | |
| F | 17 | 8.2 | | |
| Phospholipids | | | 7 | 44.2 |
| Neutral Lipids | | | 9 | 51.7 |
| Cholesterol | | | 1 | 4.2 |
| M | 174 | 85.0 | | |
| Total | 205 | 100 | 17 | 100 |

TABLE 23

| STICK WATER 1 | Kg/Hr | (%) | Kg/Hr | (%) |
|---|---|---|---|---|
| DS | 372 | 7.9 | | |
| F | 12 | 0.3 | | |
| Phospholipids | | | 0 | 0 |
| Neutral Lipids | | | 12 | 100 |
| Cholesterol | | | 0 | 0 |
| M | 4,322 | 91.8 | | |
| Total | 4,706 | 100 | 12 | 100 |

TABLE 24

| STICK WATER 2 | Kg/Hr | (%) | Kg/Hr | (%) |
|---|---|---|---|---|
| DS | 125 | 9.3 | | |
| F | 4 | 0.3 | | |
| Phospholipids | | | 0 | 0 |
| Neutral Lipids | | | 5 | 100 |
| Cholesterol | | | 0 | 0 |
| M | 1,216 | 90.4 | | |
| Total | 1,345 | 100 | 5 | 100 |

DS = Dry Solids Content
F = Fat Content
M = Moisture Content
MT = Metric Ton

The following tables shows an estimate mass balance of a production line for the product of the present invention when raw krill is within the season when fat content is high (estimated at 5%) although not necessarily the highest fat content found in raw South Antarctic Krill and with the addition or recovery of stick water.

TABLE 25

| Production | MT/Hr | Yield (%) |
|---|---|---|
| Krill Meal (with concentrate) | 2.19 | 21.9 |
| Krill Oil with Phospholipids | 0.22 | 2.2 |
| Krill Oil with Neutral Lipids | 0.07 | 0.7 |
| Total | 2.47 | 24.7 |

TABLE 26

| FRESH RAW WHOLE KRILL | Kg/Hr | (%) | Kg/Hr | (%) |
|---|---|---|---|---|
| DS | 1,800 | 18.0 | | |
| F | 500 | 5.0 | | |
| Phospholipids | | | 200 | 40.0 |
| Neutral Lipids | | | 295 | 59.0 |
| Cholesterol | | | 5 | 1.0 |
| M | 7,700 | 77.0 | | |
| Total | 10,000 | 100 | 500 | 100 |

TABLE 27

| DECANTER SOLIDS | Kg/Hr | (%) | Kg/Hr | (%) |
|---|---|---|---|---|
| DS | 1,386 | 28.7 | | |
| F | 401 | 8.3 | | |
| Phospholipids | | | 190 | 47.4 |
| Neutral Lipids | | | 208 | 51.9 |
| Cholesterol | | | 3 | 0.7 |
| M | 3,043 | 63.0 | | |
| Total | 4,830 | 100 | 401 | 100 |

TABLE 28

| PRESS CAKE | Kg/Hr | (%) | Kg/Hr | (%) |
|---|---|---|---|---|
| DS | 1,248 | 40.8 | | |
| F | 160 | 5.2 | | |
| Phospholipids | | | 104 | 65.0 |
| Neutral Lipids | | | 54 | 34.0 |
| Cholesterol | | | 2 | 1.0 |
| M | 1,652 | 54.0 | | |
| Total | 3,060 | 100 | 160 | 100 |

TABLE 29

| PRESS CAKE + SLUDGE | Kg/Hr | (%) | Kg/Hr | (%) |
|---|---|---|---|---|
| DS | 1,303 | 35.6 | | |
| F | 195 | 5.3 | | |
| Phospholipids | | | 121 | 62.4 |
| Neutral Lipids | | | 70 | 36.1 |
| Cholesterol | | | 3 | 1.5 |
| M | 2,162 | 59.1 | | |
| Total | 3,660 | 100 | 195 | 100 |

TABLE 30

| KRILL SOLUBLES | Kg/Hr | (%) | Kg/Hr | (%) |
|---|---|---|---|---|
| DS | 497 | 48.5 | | |
| F | 16 | 1.5 | | |
| Phospholipids | | | 0 | 0 |

TABLE 30-continued

| KRILL SOLUBLES | Kg/Hr | (%) | Kg/Hr | (%) |
|---|---|---|---|---|
| Neutral Lipids | | | 16 | 100 |
| Cholesterol | | | 0 | 0 |
| M | 513 | 50.0 | | |
| Total | 1,026 | 100 | 16 | 100 |

TABLE 31

| FEED TO DRIERS RCD | Kg/Hr | (%) | Kg/Hr | (%) |
|---|---|---|---|---|
| DS | 1,800 | 38.4 | | |
| F | 211 | 4.5 | | |
| Phospholipids | | | 121 | 57.6 |
| Neutral Lipids | | | 86 | 41.0 |
| Cholesterol | | | 3 | 1.4 |
| M | 2,675 | 57.1 | | |
| Total | 4,686 | 100 | 211 | 100 |

TABLE 32

| KRILL MEAL | Kg/Hr | (%) | Kg/Hr | (%) |
|---|---|---|---|---|
| DS | 1,800 | 82.4 | | |
| F | 211 | 9.6 | | |
| Phospholipids | | | 121 | 57.6 |
| Neutral Lipids | | | 86 | 41.0 |
| Cholesterol | | | 3 | 1.4 |
| M | 175 | 8.0 | | |
| Total | 2,185 | 100 | 211 | 100 |

TABLE 33

| | Kg/Hr |
|---|---|
| EVAPORATOR | 5,025 |

TABLE 34

| | Kg/Hr |
|---|---|
| EVAPORATED DRIERS RCD | 2,500 |

TABLE 35

| DECANTER LIQUID | Kg/Hr | (%) | Kg/Hr | (%) |
|---|---|---|---|---|
| DS | 414 | 8.0 | | |
| F | 99 | 1.9 | | |
| Phospholipids | | | 10 | 10.1 |
| Neutral Lipids | | | 87 | 87.9 |
| Cholesterol | | | 2 | 2.0 |
| M | 4,657 | 90.1 | | |
| Total | 5,170 | 100 | 99 | 100 |

TABLE 36

| OIL WITH NEUTRAL LIPIDS | Kg/Hr | (%) | Kg/Hr | (%) |
|---|---|---|---|---|
| Oil | 69 | 100 | | |
| Phospholipids | | | 0 | 0 |
| Neutral Lipids | | | 68 | 98.6 |
| Cholesterol | | | 1 | 1.4 |
| Total | 69 | 100 | 69 | 100 |

TABLE 37

| PRESS LIQUID | Kg/Hr | (%) | Kg/Hr | (%) |
|---|---|---|---|---|
| DS | 139 | 7.8 | | |
| F | 241 | 13.6 | | |
| Phospholipids | | | 86 | 35.7 |
| Neutral Lipids | | | 153 | 63.7 |
| Cholesterol | | | 1 | 0.6 |
| M | 1,391 | 78.6 | | |
| Total | 1,770 | 100 | 241 | 100 |

TABLE 38

| OIL WITH PHOSPHOLIPIDS | Kg/Hr | (%) | Kg/Hr | (%) |
|---|---|---|---|---|
| Oil | 220 | 100 | | |
| Phospholipids | | | 79 | 35.7 |
| Neutral Lipids | | | 140 | 63.7 |
| Cholesterol | | | 1 | 0.5 |
| Total | 220 | 100 | 220 | 100 |

TABLE 39

| SLUDGE 1 | Kg/Hr | (%) | Kg/Hr | (%) |
|---|---|---|---|---|
| DS | 41 | 10.5 | | |
| F | 18 | 4.5 | | |
| Phospholipids | | | 10 | 56.1 |
| Neutral Lipids | | | 7 | 38.3 |
| Cholesterol | | | 1 | 5.6 |
| M | 336 | 85.0 | | |
| Total | 395 | 100 | 18 | 100 |

TABLE 40

| SLUDGE 2 | Kg/Hr | (%) | Kg/Hr | (%) |
|---|---|---|---|---|
| DS | 14 | 6.8 | | |
| F | 17 | 8.2 | | |
| Phospholipids | | | 7 | 44.2 |
| Neutral Lipids | | | 9 | 53.5 |
| Cholesterol | | | 0 | 2.4 |
| M | 174 | 85.0 | | |
| Total | 205 | 100 | 17 | 100 |

TABLE 41

| STICK WATER 1 | Kg/Hr | (%) | Kg/Hr | (%) |
|---|---|---|---|---|
| DS | 372 | 7.9 | | |
| F | 12 | 0.3 | | |
| Phospholipids | | | 0 | 0 |

TABLE 41-continued

| STICK WATER 1 | Kg/Hr | (%) | Kg/Hr | (%) |
|---|---|---|---|---|
| Neutral Lipids |  |  | 12 | 100 |
| Cholesterol |  |  | 0 | 0 |
| M | 4,322 | 91.8 |  |  |
| Total | 4,706 | 100 | 12 | 100 |

TABLE 42

| STICK WATER 2 | Kg/Hr | (%) | Kg/Hr | (%) |
|---|---|---|---|---|
| DS | 125 | 9.3 |  |  |
| F | 4 | 0.3 |  |  |
| Phospholipids |  |  | 0 | 0 |
| Neutral Lipids |  |  | 4 | 100 |
| Cholesterol |  |  | 0 | 0 |
| M | 1,216 | 90.4 |  |  |
| Total | 1,345 | 100 | 4 | 100 |

Example 3

Composition of the Neutral Lipid Enriched Krill Oil of the Present Invention

TABLE 43

| Neutral Lipids | | % w/w |
|---|---|---|
|  | Triglycerides | 84.6 |
|  | Diglycerides | 4.9 |
|  | Free Fatty Acids | ND |
|  | Monoglycerides | ND |
|  | Total | 89.5 |
| Phospholipids | ND | <0.5 |
| alpha-Tocopherol |  | 0.7 |

| Fatty acid Analysis | FAME (Fatty Acid Methyl Ester) | % w/w |
|---|---|---|
| Total Sample | 8:0 | 0.0 |
|  | 9:0 | 0.0 |
|  | 10:0 | 0.0 |
|  | 11:0 | 0.0 |
|  | 12:0 | 0.3 |
|  | 13:0 | 0.0 |
|  | 14:0 | 16.3 |
|  | 15:0 | 0.5 |
|  | 16:0 | 18.2 |
|  | 17:0 | 0.3 |
|  | 18:0 | 1.5 |
|  | 19:0 | 1.0 |
|  | 20:0 | 0.0 |
|  | 22:0 | 0.1 |
|  | 23:0 | 0.0 |
|  | 24:0 | 0.0 |
|  | Saturated Total | 38.3 |
|  | 11:1 | 0.0 |
|  | 13:1 | 0.0 |
|  | 14:1 | 0.2 |
|  | 16:1 | 9.5 |
|  | 17:1 | 1.2 |
|  | 18:1 cis | 14.6 |
|  | 18:1 trans | 6.4 |
|  | 20:1 | 1.2 |
|  | 22:1 | 0.1 |
|  | 24:1 | 0.0 |
|  | Monounsaturated Total | 33.2 |
|  | 18:2 | 1.3 |
|  | 18:3 (6,9,12) | 0.2 |
|  | 18:3 (9,12,15) | 0.6 |
|  | 20:2 | 0.0 |
|  | 20:3 (8,11,14) | 0.0 |
|  | 20:4 | 0.0 |
|  | 20:3 (5,8,11) | 0.2 |
|  | 20:5 | 3.3 |
|  | 22:2 | 0.2 |
|  | 22:3 | 0.0 |
|  | 22:4 | 0.0 |
|  | 22:5 N3 | 0.1 |
|  | 22:6 | 1.1 |
|  | Polyunsaturated Total | 7.1 |
|  | Total All | 78.6 |

ND = Not Detected

Example 4

Composition of the Phospholipids'Enriched Krill Oil of the Present Invention

TABLE 44

| Lipid Class | Composition (% total lipid)* |
|---|---|
| Sterol esters | 1.2 |
| Triacylglycerols | 45.6 |
| Free fatty acids | 3.4 |
| Cholesterol/sterols | 4.3 |
| Diacylglycerols** | 7.7 |
| Monoacylglycerols | 0.9 |
| Total neutral lipids | 63.1 |
| Phosphatidylcholine | 25.2 |
| Phosphatidylethanolamine | 7.3 |
| Phosphatidylserine | 1.5 |
| Phosphatidylinositol | 1.3 |
| Phosphatidylglycerol + cardiolipin | 1.0 |
| Lysophosphatidylcholine | 0.6 |
| Total polar lipids | 36.9 |

Values are means of duplicate analyses
*as determined by HPTLC/densitometry.
**contains pigments.

Fatty Acid Composition of Total Lipid

TABLE 45

|  | % total fatty acids |
|---|---|
| 14:0 | 12.55 |
| br 15:0 | 0.28 |
| 15:0 | 0.48 |
| br 16:0 | 0.13 |
| 16:0 | 21.67 |
| br 17:0 | 0.43 |
| 17:0 | 0.10 |
| 18:0 | 1.47 |
| 20:0 | 0.29 |
| Total saturated | 37.39 |
| 16:1n-9 | 0.38 |
| 16:1n-7 | 6.81 |
| 16:1 isomer | 0.60 |
| 17:1n-8 | 0.29 |
| 18:1n-9 | 12.21 |
| 18:1n-7 | 7.43 |
| 20:1n-11 | 0.07 |
| 20:1n-9 | 0.93 |
| 20:1n-7 | 0.42 |
| 22:1n-11 | 0.53 |

TABLE 45-continued

| | % total fatty acids |
|---|---|
| 22:1n-9 | 0.14 |
| 24:1n.9 | 0.21 |
| Total monounsaturated | 30.02 |
| 18:2n-6 | 1.74 |
| 18:3n-6 | 0.17 |
| 20:2n-6 | 0.08 |
| 20:3n-6 | 0.10 |
| 20.4n-6 | 0.33 |
| Total n-6 PUFA (Polyunsaturated Fatty Acids) | 2.43 |
| 18:3n-3 | 0.98 |
| 18:4n-3 | 3.24 |
| 20:3n-3 | 0.10 |
| 20:4n-3 | 0.34 |
| 20:5n-3 | 15.20 |
| 22:5n-3 | 0.40 |
| 22:6n-3 | 7.55 |
| Total n-3 PUFA | 27.81 |
| 16:2 | 0.69 |
| 16:3 | 0.27 |
| 16:4 | 1.38 |
| Total 16C PUFA | 2.35 |
| TOTAL PUFA | 32.59 |
| Total | 100.00 |

Values are means of duplicate analyses

Limit of quantification (LOQ) for fatty acid analysis=0.06%

Fatty Acid Composition of Phosphatidylcholine/Lysophosphatidylcholine

TABLE 46

| | % total fatty acids |
|---|---|
| 14:0 | 2.79 |
| br 15:0 | 0.10 |
| 15:0 | 0.37 |
| br 16:0 | 0.12 |
| 16:0 | 27.17 |
| br 17:0 | 0.47 |
| 17:0 | 0.15 |
| 18:0 | 1.04 |
| 20:0 | 0.22 |
| Total saturated | 32.44 |
| 16:1n-9 | 0.15 |
| 16:1n-7 | 1.73 |
| 16:1 isomer | 0.28 |
| 17:1n-8 | 0.14 |
| 18:1n-9 | 4.46 |
| 18:1n-7 | 5.14 |
| 20:1n-11 | <LOQ |
| 20:1n-9 | 0.60 |
| 20:1n-7 | 0.27 |
| 22:1n-11 | 1.12 |
| 22:1n-9 | 0.50 |
| 24:1n.9 | 0.46 |
| Total monounsaturated | 14.87 |
| 18:2n-6 | 1.55 |
| 18:3n-6 | 0.27 |
| 20:2n-6 | <LOQ |
| 20:3n-6 | 0.10 |
| 20.4n-6 | 0.59 |
| Total n-6 PUFA | 2.50 |
| 18:3n-3 | 1.05 |
| 18:4n-3 | 1.98 |
| 20:3n-3 | 0.14 |
| 20:4n-3 | 0.47 |
| 20:5n-3 | 31.50 |

TABLE 46-continued

| | % total fatty acids |
|---|---|
| 22:5n-3 | 0.63 |
| 22:6n-3 | 14.09 |
| Total n-3 PUFA | 49.87 |
| 16:2 | 0.10 |
| 16:3 | 0.12 |
| 16:4 | 0.11 |
| Total 16C PUFA | 0.33 |
| TOTAL PUFA | 52.70 |
| Total | 100.00 |

Values are means of duplicate analyses

Limit of quantification (LOQ) for fatty acid analysis=0.06%

Fatty Acid Composition of Phosphatidylethanolamine

TABLE 47

| | % total fatty acids |
|---|---|
| 14:0 | 0.56 |
| br 15:0 | 0.07 |
| 15:0 | 0.20 |
| br 16:0 | 0.17 |
| 16:0 | 14.65 |
| br 17:0 | 0.39 |
| 17:0 | 0.83 |
| 18:0 | 1.24 |
| 20:0 | <LOQ |
| Total saturated | 18.11 |
| 16:1n-9 | 0.25 |
| 16:1n-7 | 0.61 |
| 16:1 isomer | 0.27 |
| 17:1n-8 | <LOQ |
| 18:1n-9 | 3.92 |
| 18:1n-7 | 14.03 |
| 20:1n-11 | <LOQ |
| 20:1n-9 | 0.48 |
| 20:1n-7 | 0.10 |
| 22:1n-11 | <LOQ |
| 22:1n-9 | <LOQ |
| 24:1n.9 | 0.08 |
| Total monounsaturated | 19.79 |
| 18:2n-6 | 0.95 |
| 18:3n-6 | 0.49 |
| 20:2n-6 | 0.15 |
| 20:3n-6 | 0.15 |
| 20.4n-6 | 1.35 |
| Total n-6 PUFA | 3.10 |
| 18:3n-3 | 0.38 |
| 18:4n-3 | 0.25 |
| 20:3n-3 | 0.14 |
| 20:4n-3 | 0.42 |
| 20:5n-3 | 23.35 |
| 22:5n-3 | 0.75 |
| 22:6n-3 | 33.12 |
| Total n-3 PUFA | 58.43 |
| 16:2 | 0.14 |
| 16:3 | 0.17 |
| 16:4 | 0.27 |
| Total 16C PUFA | 0.58 |
| TOTAL PUFA | 62.10 |
| Total | 100.00 |

Values are means of duplicate analyses

Limit of quantification (LOQ) for fatty acid analysis=0.06%

Fatty Acid Composition of Triacylglycerol

TABLE 48

| | % total fatty acids |
|---|---|
| 14:0 | 20.52 |
| br 15:0 | 0.42 |
| 15:0 | 0.61 |
| br 16:0 | 0.15 |
| 16:0 | 21.85 |
| br 17:0 | 0.48 |
| 17:0 | 0.09 |
| 18:0 | 1.67 |
| 20:0 | 0.31 |
| Total saturated | 46.11 |
| 16:1n-9 | 0.21 |
| 16:1n-7 | 9.90 |
| 16:1 isomer | 0.72 |
| 17:1n-8 | 0.36 |
| 18:1n-9 | 16.76 |
| 18:1n-7 | 8.26 |
| 20:1n-11 | 0.08 |
| 20:1n-9 | 1.14 |
| 20:1n-7 | 0.55 |
| 22:1n-11 | 0.24 |
| 22:1n-9 | 0.11 |
| 24:1n.9 | <LOQ |
| Total monounsaturated | 38.32 |
| 18:2n-6 | 1.79 |
| 18:3n-6 | 0.22 |
| 20:2n-6 | <LOQ |
| 20:3n-6 | <LOQ |
| 20:4n-6 | 0.08 |
| Total n-6 PUFA | 2.09 |
| 18:3n-3 | 0.86 |
| 18:4n-3 | 3.40 |
| 20:3n-3 | 0.07 |
| 20:4n-3 | 0.17 |
| 20:5n-3 | 4.05 |
| 22:5n-3 | 0.20 |
| 22:6n-3 | 1.49 |
| Total n-3 PUFA | 10.22 |
| 16:2 | 1.00 |
| 16:3 | 0.37 |
| 16:4 | 1.88 |
| Total 16C PUFA | 3.25 |
| TOTAL PUFA | 15.57 |
| Total | 100.00 |

Values are means of duplicate analyses

Limit of quantification (LOQ) for fatty acid analysis=0.06%

Lipid class composition of lipid samples and fatty acid compositions of individual lipids were determined by high performance thin-layer chromatography (HPTLC) and quantitation using a scanning densitometry according to Henderson and Tocher (Henderson, R. J. and Tocher, D. R. (1992) Thin-layer chromatography. In Lipid Analysis: A Practical Approach (Hamilton, R. J., and Hamilton, S., eds.) pp. 65-111, Oxford University Press, Oxford).

Example 5

Other Characteristics of the Krill Oil of the Present Invention

TABLE 49

| | Composition |
|---|---|
| Vitamin E Composition (*) in mg/Kg | 13.80 |
| Peroxide Value (*) in Meq/Kg | 0.0 |
| Iodine Value (IV) (**) (g/100 g) | 150.37 |

(*) Calculated in Duplicate
(**) Calculated by the modification of Ham et al. (J.A.O.C.S. 75, 1445-1446(1998)) of the AOCS recommended practice Cd 1c-85.

Example 6

Heavy Metals Content for the Krill Oil of the Present Invention

TABLE 50

| Heavy Metal | | Present Invention %/w | Neptune Bioressouces %/w | 999 (Triple Nine) %/w |
|---|---|---|---|---|
| Antimony | ppm | <0.02 | <0.03 | <0.02 |
| Arsenic | ppm | <0.05 | 2.31 | 4.49 |
| Bismuth | ppm | <0.02 | 0.17 | <0.02 |
| Cadmium | ppm | <0.02 | <0.03 | 0.07 |
| Copper | ppm | <0.04 | 0.21 | 13.1 |
| Lead | ppm | <0.02 | 0.09 | 0.27 |
| Mercury | ppm | <0.02 | <0.03 | <0.04 |
| Molybdenum | ppm | <0.02 | <0.03 | 0.06 |
| Silver | ppm | <0.02 | <0.03 | 0.45 |
| Tin | ppm | <0.02 | <0.03 | 0.05 |
| Total | ppm | <0.05 | 2.78 | 18.49 |

Example 7

Composition of the Low Fat Krill Meal of the Present Invent with Krill Captured During South Antarctic's Krill Fatty Period

TABLE 51

| Compounds | Value |
|---|---|
| Moisture (%) | 8.0 |
| Proteins (%) | 66.1 |
| Lipids (%) | 12.1 |
| Ash (%) | 9.3 |
| Astaxanthin (mg/Kg) | 119 |

Example 8

Dietary Supplement (Nutraceutical/Dietary) Based on Krill Oil

It is described a food rich in fat material for complementing essential fatty acids. Such food was formulated in cookie form elaborated using krill oil, krill meal or krill dried complex.

In a bowl 400 g Quaker was mixed with 100 g of flour, 500 g of sugar, 1 egg, 150 mL of krill oil of this invention and 10 mL of vanilla extract. Once completely homogenized, the cookies were molded weighing each 25 g, and were baked at 160° C. for 15 min as longer cooking times destroys the astaxanthin.

The amount of cookies used in the diets will depend on the amount of essential fatty acids such as 18:2 and 18:3 required, and the necessary calories.

Example 9

Photoprotector

The krill oil prepared as described in the examples 3 and 4 can be used for the preparation of tanning creams and tanning oils for solar protection.

A) Tanning Creams.

In this example are described two tanning creams, one with solar protection factor 5 (SPF 5) and one with solar protection factor 20 (SPF 20).

TABLE 52

| Component | Composition per 100 g of Tanning Cream | |
|---|---|---|
| | SPF 5 | SPF 20 |
| Krill Oil | 5.00 g | 5.00 g |
| Carbopol 940 | 0.25 g | 0.25 g |
| Cetilic alcohol | 0.50 g | 0.50 g |
| Methyl paraben | 0.15 g | 0.15 g |
| Estearic acid III pr. | 2.00 g | 2.00 g |
| Propyl paraben | 0.15 g | 0.15 g |
| Panalen | 5.00 g | 5.00 g |
| EDTA disodium | 0.10 g | 0.10 g |
| Triethanolamine | 0.50 g | 0.50 g |
| Propylenglycol | 2.50 g | 2.50 g |
| Octylmethoxycinamate | — | 7.50 g |
| Benzophenone 3 | — | 3.00 g |
| Titanium dioxide | — | 0.50 g |
| Imidazolidinilurea | 0.30 g | 0.30 g |
| Glyceril monoestearate | 1.00 g | 1.00 g |
| Natural essence | c.s. | c.s. |
| Isopropyl miristate | 2.00 g | 2.00 g |
| Water | c.s. | c.s. |

B) Tanning Oil:

The following description corresponds to tanning oil that contains krill oil as the unique sun-blocking agent.

TABLE 53

| Compound | Composition per 100 g of Tanning Oil |
|---|---|
| Cosmetic liquid Vaseline | 80.0 g |
| Hydrogenated polybutenes | 5.0 g |
| Krill oil | 14.7 g |
| Essence | 0.3 g |

Example 10

Cosmetic Products Based on Krill Oil

Since krill oil has several biological activities, such as being a pigmentant, antioxidant capacity, EPA and essential fatty acids content, it is possible to design cosmetic products.

A) Moisturizing Cream.

TABLE 54

| Compound | Composition per 100 g of Moisturizing Cream |
|---|---|
| Estearic acid | 1.0 g |
| Anionic glyceril monoestearate A.E. | 0.7 g |
| Neutral glyceril monoesteararte | 0.5 g |
| Hydrogenated polybutenes | 3.2 g |
| Krill oil | 10.0 g |
| Propylenglycol | 2.0 g |
| Isopropyl miristate | 1.5 g |
| Carboxyvinyl polymer | 0.3 g |
| Propylparabene | 0.1 g |
| Methylparabene | 0.1 g |
| Essence | 0.3 g |
| EDTA disodium | 0.2 g |
| Triethanolamine 99% | 1.2 g |
| Demineralized water | 78.9 g |

B) Powder Makeup.

In this example a base formula for the elaboration of powder makeup that contains 10% (w/w) krill oil is described.

TABLE 55

| Compound | Composition per 100 g of Makeup |
|---|---|
| Talcum powder | 52.56 g |
| Krill oil | 10.00 g |
| Mica:Titanuim dioxide (2:1) | 26.00 g |
| Magnesium estearate | 3.50 g |
| Isopropyl miristate | 1.60 g |
| Oleic alcohol | 2.60 g |
| Octylpalmitate | 3.40 g |
| Methylparabene | 0.17 g |
| Propylparabene | 0.17 g |

C) Powder Eye Shadow.

In this example a base formula for the elaboration of a powder eyeshadow that contains 10% (w/w) krill oil of this invention is described.

TABLE 56

| Compound | Composition per 100 g of Eye Shadow |
|---|---|
| Talcum powder | 51.46 g |
| Krill oil | 10.00 g |
| Mica:Titanium dioxide (3:1) | 27.00 g |
| Magnesium estearate | 3.50 g |
| Isopropyl miristate | 1.60 g |
| Oleic alcohol | 2.60 g |
| Octylpalmitate | 3.50 g |
| Methylparabene | 0.17 g |
| Propylparabene | 0.17 g |

D) Cream Eye Shadow

In this example a base formula for the elaboration of a cream eyeshadow that contains 5.7% (w/w) krill oil of this invention is described.

TABLE 57

| Compound | Composition per 100 g of Eye Shadow |
|---|---|
| Talcum powder | 4.0 g |
| Estearic acid | 9.5 g |
| Isoestearic acid | 1.9 g |
| Krill Oil | 5.7 g |
| Titanium dioxide | 1.9 g |

TABLE 57-continued

| Compound | Composition per 100 g of Eye Shadow |
| --- | --- |
| Aluminum and magnesium silicate | 3.6 g |
| Propylenglycol | 16.1 g |
| Triethanolamine | 11.0 g |
| Methylparabene | 0.2 g |
| Propylparabene | 0.2 g |
| Deionized water | 45.9 g |

E) Compact Powder.

In this example a base formula for the elaboration of a compact powder that contains 10% (w/w) krill oil of the present invention is described.

TABLE 58

| Compound | Composition per 100 g of Compact Powder |
| --- | --- |
| Kaolin | 32.0 g |
| Krill Oil | 10.0 g |
| Mica:Titanium dioxide (2:1) | 1.6 g |
| Magnesium estearate | 4.1 g |
| Octylpalmitate | 2.5 g |
| Propylparabene | 0.5 g |
| Talcum powder | 49.3 g |

F) Lipstick.

In this example a base formula for a lipstick that contains 3% (w/w) krill oil is described.

TABLE 59

| Compound | Composition per 100 g of Lipstick |
| --- | --- |
| Castor Oil | 42.04 g |
| Krill Oil | 3.00 g |
| Oleic alcohol | 2.60 g |
| Lanolin | 25.00 g |
| Sorbitan monoestearate | 1.30 g |
| Ozokerite | 4.50 g |
| Carnauba wax | 5.20 g |
| Beeswax | 5.60 g |
| Estearic acid | 4.90 g |
| Candle wax | 5.60 g |
| Methylparabene | 0.13 g |
| Propylparabene | 0.13 g |

Example 11

Pharmaceutical Products Based on Krill Oil

Krill and/or marine oil has been shown to decrease cholesterol in vivo. It also inhibits platelet adhesion and plaque formation and reduces vascular endothelial inflammation in a patient. It can offer hypertension prophylaxis. It prevents oxidation of low-density lipoprotein. It may have an inhibitory effect on the secretion of VLDL due to increased intracellular degradation of apo B-100. It also offers a post-myocardial infarction prophylaxis because of its ability to decrease CIII apolipoprotein B, to decrease CIII non-apolipoprotein B lipoproteins and to increase antithrombin III levels. Krill and/or marine oil is suitable for prophylactic usage against cardiovascular disease in human where cardiovascular disease relates to coronary artery disease, hyperlipidemia, hypertension, ischemic disease (relating to angina, myocardial infarction, cerebral ischemia, shock without clinical or laboratory evidence of ischemia, arrhythmia).

A pharmaceutical composition of krill oil of this invention comprises capsules containing 1 mL of krill oil described in examples 3 and 4. A pharmaceutical composition of krill dried complex of this invention comprises capsules containing 1 to 5 g of krill dried complex.

We claim:

1. A solvent-free method for producing krill oil comprising:
   a) cooking whole fresh krill or a krill extract at a temperature of at least 90° C. to denature the proteins in the whole fresh krill or krill extract while substantially avoiding emulsification to produce a cooked krill or cooked krill extract;
   b) separating the cooked krill or cooked krill extract from step a) using a decanter to obtain a partially de-fatted and de-watered solid and a decanter liquid;
   c) squeezing the partially de-fatted and de-watered solid from step b) onto a screw press or screw conveyor to obtain a press liquid and a solid fraction;
   d) separating the press liquid from step c) to obtain krill oil enriched in phospholipids;
   e) separating the decanter liquid from step b) to obtain krill oil enriched in neutral lipids, and water; and
   f) drying the press liquid from step c) to obtain a dried complex of human-grade krill which contains krill oil in combination with phospholipids, DHA, EPA, proteins and astaxanthin,
   wherein steps a) through f) are carried out while substantially avoiding emulsification.

2. The method of claim 1, wherein the cooking of step a) is carried out using indirect and/or direct steam heating or another heating system.

3. The method of claim 2, wherein the heating system has a low rotation speed of about 1-100 rpm.

4. The method of claim 1, wherein a torque of the decanter of step b) is about 1-10 kNn.

5. The method of claim 1, wherein the decanter of step b) has a speed of 100-10,000 rpm.

6. The method of claim 1, wherein the decanter of step b) is selected from the group consisting of a traditional decanter, a two-phase decanter, a triple-phase decanter, and any other decanter that minimizes agitation, grinding and/or mincing of the krill.

7. The method of claim 1, wherein the separating of steps d) and e) is carried out first in a separator centrifuge and then in a purifier separator centrifuge, wherein from step d) is obtained krill oil enriched in phospholipids and from step e) is obtained krill oil enriched in neutral lipids, wherein each krill oil type has a separate and exclusive separator centrifuge and purifier separator centrifuge.

8. The method of claim 1, wherein the squeezing of the partially de-fatted and de-watered solid in step c) is carried out by feeding the solid to a screw pump or a screw conveyor or any other feeding system avoiding agitation, and pressing the solid using a screw press with a speed of about 2-10 rpm, and wherein the temperature of the fed solid is about 90-96° C.

9. The method of claim 1, wherein the screw press is selected from the group consisting of a simple screw press, a twin-screw press and any other screw press.

10. The method of claim 1, wherein the separating of the press liquid in step d) is carried out by pumping the press liquid to a separator centrifuge at a temperature of about 25-121° C.

11. The method of claim 1, wherein the solid fraction obtained in step c) is further processed to obtain low-fat krill meal.

12. The method of claim 1, wherein antioxidants and/or preservatives are added to the obtained krill oil, optionally under a nitrogen barred layer.

13. The method of claim 1, wherein the whole flesh krill and/or fraction thereof of step a) is flesh raw material.

* * * * *